(12) United States Patent
Yokoi et al.

(10) Patent No.: US 8,482,288 B2
(45) Date of Patent: Jul. 9, 2013

(54) PARTICULATE MATTER DETECTION DEVICE AND INSPECTION METHOD OF THE PARTICULATE MATTER DETECTION DEVICE

(75) Inventors: Shoji Yokoi, Nagoya (JP); Takayuki Sakurai, Kakamigahara (JP); Tatsuya Okayama, Wako (JP); Masanobu Miki, Wako (JP); Keizo Iwama, Wako (JP); Makoto Hattori, Wako (JP); Hidetaka Ozawa, Wako (JP)

(73) Assignees: NGK Insulators, Ltd., Nagoya (JP); Honda Motor Co., Ltd., Minato-Ku (JP)

(*) Notice: Subject to any disclaimer, the term of this patent is extended or adjusted under 35 U.S.C. 154(b) by 381 days.

(21) Appl. No.: 12/979,455

(22) Filed: Dec. 28, 2010

(65) Prior Publication Data
US 2011/0163761 A1 Jul. 7, 2011

(30) Foreign Application Priority Data
Jan. 7, 2010 (JP) .................................. 2010-002300

(51) Int. Cl.
*F02P 17/00* (2006.01)
(52) U.S. Cl.
USPC .......................................... 324/378; 123/479

(58) Field of Classification Search
USPC .................................... 324/378, 402; 123/479
See application file for complete search history.

(56) References Cited

U.S. PATENT DOCUMENTS

| 5,048,490 A * | 9/1991 | Nakaniwa .................... 123/479 |
| 2006/0107730 A1 | 5/2006 | Schumann | |

FOREIGN PATENT DOCUMENTS

| JP | 60-123761 A1 | 7/1985 |
| JP | 2006-503270 A1 | 1/2006 |
| JP | 2009-186278 A1 | 8/2009 |

* cited by examiner

*Primary Examiner* — Vincent Q Nguyen
(74) *Attorney, Agent, or Firm* — Burr & Brown

(57) ABSTRACT

The particulate matter detection device of the present invention is a particulate matter detection device 100 including an electrode portion 21 and detection means 23 for detecting an electrical characteristic of the electrode portion 21, whereby a particulate matter 36 contained in an exhaust gas 32 is detected on the basis of a change of the electrical characteristic due to the particulate matter 36 attached to the electrode portion 21. The particulate matter detection device i00 further includes removal means 25 and abnormality judgment means 26 for comparing an initial electrical characteristic in a use initial state of the device with the electrical characteristic measured in a state where the particulate matter 36 attached to the surface of the electrode portion 21 is removed by the removal means 25, to judge whether or not the particulate matter detection device i00 has an abnormality.

19 Claims, 6 Drawing Sheets

PARTICULATE MATTER DETECTION DEVICE AND INSPECTION METHOD OF THE PARTICULATE MATTER DETECTION DEVICE

BACKGROUND OF THE INVENTION

1. Field of the Invention

The present invention relates to a particulate matter detection device and an inspection method of the particulate matter detection device. More particularly, it relates to a particulate matter detection device which can judge whether or not detection of a particulate matter by the particulate matter detection device is normally performed and satisfactorily inspect the device for break-down or defect of the device, and an inspection method of the particulate matter detection device.

2. Description of the Related Art

A flue exhaust gas or a diesel engine exhaust gas contains a particulate matter (PM) such as soot, which has been a cause for air pollution. To remove the particulate matter, a filter (a diesel particulate filter: DPF) made of a ceramic material or the like has broadly been used. The ceramic DPF can be used for a long period of time, but defects such as cracks and melting damages occur owing to thermal deterioration or the like sometimes, and a micro amount of particulate matter might leak. In case of the occurrence of such a defect, it is remarkably important from the viewpoint of prevention of the air pollution to readily detect the occurrence of the defect and recognize an abnormality of a device.

Examples of a method of detecting the occurrence of such a defect include a method of disposing a particulate matter detection device on the downstream side of the DPF (e.g., see Patent Document 1).

In the invention disclosed in Patent Document 1, a particulate matter is charged by corona discharge to measure an ion current, thereby measuring the amount of the particulate matter. In this way, in the method of charging the particulate matter to measure the ion current thereof, the ion current which charges the particulate matter is weak, and hence a large-scale detection circuit is necessary for detecting the weak ion current, whereby the method becomes expensive. Moreover, when an exhaust gas has a high flow rate, it is difficult to effectively charge the particulate matter. Therefore, the measured value of the particulate matter becomes smaller than a value of the amount of the particulate matter actually contained in the exhaust gas, so that an error of the value increases.

To solve such a problem, for example, there has been suggested a particulate matter detection device or the like comprising a unidirectionally long detection device main body having one end portion provided with one through hole, and at least a pair of electrodes embedded in a wall of the through hole and covered with a dielectric material. A particulate matter in an exhaust gas can electrically be adsorbed by the wall face of the through hole, and a change of electrical characteristics of the wall of the through hole can be measured to detect a mass of the particulate matter adsorbed by the wall face of the through hole (see Patent Document 2).

Moreover, there has been suggested an inspection method or system for confirming a normal operation of a detection device which measures a size of an ion current to measure a particulate matter in an exhaust gas as disclosed in Patent Document 1 (e.g., see Patent Document 3).

[Patent Document 1] JP-A-60-123761
[Patent Document 2] JP-A-2009-186278
[Patent Document 3] JP-A-2006-503270

SUMMARY OF THE INVENTION

A particulate matter detection device disclosed in Patent Documents 1 and 2 is installed on the downstream side of an exhaust gas treatment device such as a DPF to judge whether or not purification of the exhaust gas, i.e., removal of a particulate matter is normally performed by the exhaust gas treatment device. When the exhaust gas treatment device normally functions, needless to say, any particulate matter is not detected, and any electric signal or the like to be detected when detecting the particulate matter usually is not detected.

However, even when such a particulate matter detection device for confirming 'any particulate matter is not detected' cannot recognize any signal of the detection of the particulate matter owing to a detection device defect or the like, the detection device sometimes indicates a behavior similar to that in a case where the exhaust gas treatment device normally functions. There is a rising need to inspect whether or not the particulate matter detection device normally functions before or while using the particulate matter detection device.

For example, in the particulate matter detection device disclosed in Patent Document 2, when disconnection or break-down of a measurement electrode, short circuit of a pair of measurement electrodes, break-down of a dielectric material or the like occurs, the particulate matter cannot normally be detected, which causes a problem that discharge of the particulate matter is missed or that a large error is generated in a quantitatively measured value. In particular, this particulate matter detection device can detect a remarkably micro amount of the particulate matter, and hence it becomes especially important to confirm a level (i.e., zero point) at which any particulate matter is not detected. It is to be noted that in the inspection method and system disclosed in Patent Document 3, the detection device as an inspection target has a different mechanism, and hence it is impossible to perform this invention with respect to the particulate matter detection device disclosed in Patent Document 2 or the like.

The present invention has been developed in view of the above problem, and an object thereof is to provide a particulate matter detection device which detects a particulate matter in an exhaust gas and which can judge whether or not the detection of the particulate matter is normally performed (e.g., self-diagnosis) and satisfactorily inspect the device for break-down or defect, and to provide an inspection method of the particulate matter detection device.

To achieve the above object, according to the present invention, there are provided a particulate matter detection device and an inspection method of the particulate matter detection device as follows.

[1] A particulate matter detection device which comprises: an electrode portion disposed in an exhaust system of an internal combustion engine; and detection means for detecting an electrical characteristic of the electrode portion, whereby a particulate matter contained in an exhaust gas passing through the exhaust system is detected on the basis of a change of the electrical characteristic due to the particulate matter attached to the electrode portion, the particulate matter detection device further comprising: removal means for removing the particulate matter attached to the electrode portion; and abnormality judgment means for measuring the electrical characteristic of the electrode portion in a use initial state where any particulate matter is not attached to the electrode portion, to obtain the electrical characteristic as an initial electrical characteristic, and measuring the electrical characteristic of the electrode portion in a state where the particulate matter attached to the surface of the electrode portion is removed by the removal means to start the detection of the particulate matter by the particulate matter detection device, and comparing a value of the measured electrical characteristic with a value of the initial electrical characteristic, to judge whether or not the particulate matter detection device has an abnormality.

[2] The particulate matter detection device according to [1], wherein the electrical characteristic compared by the abnormality judgment means is a capacitance or a resistance.

[3] The particulate matter detection device according to [1] or [2], wherein the removal means comprises a heater which heats the inside of the device.

[4] The particulate matter detection device according to any one of [1] to [3], wherein at least a part of the electrode portion is covered with a dielectric material, and the abnormality judgment means measures the electrical characteristic of the electrode portion while raising a temperature of the dielectric material, and further inspects the device for disconnection or contact defect of the electrode portion or break-down of the dielectric material from the change of the electrical characteristic to be measured.

[5] The particulate matter detection device according to [4], wherein it is judged that the abnormality is the disconnection or contact defect of the electrode portion in a case where the electrical characteristic to be measured does not change with respect to temperature change of the dielectric material.

[6] The particulate matter detection device according to any one of [1] to [5], wherein at least a part of the electrode portion is covered with a dielectric material, and during the measurement of the electrical characteristic of the electrode portion, the abnormality judgment means measures the electrical characteristic while changing a frequency of a voltage to be applied to the electrode portion, and inspects the device for break-down of the dielectric material in accordance with transition of the electrical characteristic to be measured.

[7] The particulate matter detection device according to any one of [1] to [6], wherein the initial electrical characteristic is beforehand set to the abnormality judgment means, and the abnormality judgment means compares a value of the set initial electrical characteristic with a value of the measured electrical characteristic to judge whether or not the particulate matter detection device has the abnormality.

[8] The particulate matter detection device according to any one of [1] to [7], further comprising: a unidirectionally long detection device main body having one end portion provided with at least one through hole, wherein the electrode portion comprises at least a pair of measurement electrodes disposed in the inner side surface or inside of one wall of the through hole; and at least a pair of dust collecting electrodes embedded in facing walls of the through hole, respectively, and outside a position of the wall of the through hole where the pair of measurement electrodes are embedded, and covered with the dielectric material.

[9] The particulate matter detection device according to [8], wherein the value of the initial electrical characteristic is compared with the value of the measured electrical characteristic to inspect the device for at least one abnormality selected from the group consisting of disconnection, contact defect and break-down of the measurement electrode, short circuit of the pair of measurement electrodes and break-down of the dielectric material.

[10] An inspection method of a particulate matter detection device comprising: an electrode portion disposed in an exhaust system of an internal combustion engine; and detection means for detecting an electrical characteristic of the electrode portion, whereby a particulate matter contained in an exhaust gas passing through the exhaust system is detected on the basis of a change of the electrical characteristic due to the particulate matter attached to the electrode portion, the inspection method comprising the steps of: measuring the electrical characteristic of the electrode portion in a use initial state where any particulate matter is not attached to the electrode portion, to obtain the electrical characteristic as an initial electrical characteristic; measuring the electrical characteristic of the electrode portion in a state where the particulate matter attached to the electrode portion of the particulate matter detection device installed in a through channel through which the exhaust gas passes is removed to start the detection of the particulate matter by the particulate matter detection device; and comparing a value of the measured electrical characteristic with a value of the initial electrical characteristic, to judge whether or not the particulate matter detection device has the abnormality.

[11] The inspection method of the particulate matter detection device according to [10], which uses the particulate matter detection device further comprising removal means for removing the particulate matter attached to the device.

[12] The inspection method of the particulate matter detection device according to [10] or [11], further comprising the steps of measuring a capacitance or a resistance as the electrical characteristic.

[13] The inspection method of the particulate matter detection device according to any one of [10] to [12], which uses the particulate matter detection device further comprising a heater which heats the inside of the device.

[14] The inspection method of the particulate matter detection device according to any one of [10] to [13], which uses the particulate matter detection device comprising the electrode portion having at least a part thereof covered with a dielectric material, further comprising the steps of measuring the electrical characteristic of the electrode portion while raising a temperature of the dielectric material, to further inspect the device for disconnection or contact defect of the electrode portion or break-down of the dielectric material from a change of the electrical characteristic to be measured.

[15] The inspection method of the particulate matter detection device according to [14], further comprising the steps of judging that the abnormality is the disconnection or contact defect of the electrode portion in a case where the electrical characteristic to be measured does not change with respect to temperature change of the dielectric material.

[16] The inspection method of the particulate matter detection device according to any one of [10] to [15], which uses the particulate matter detection device comprising the electrode portion having at least a part thereof covered with a dielectric material, wherein the step of measuring the electrical characteristic of the electrode portion measures the electrical characteristic while changing a frequency of a voltage to be applied to the electrode portion, to inspect the device for break-down of the dielectric material in accordance with transition of the electrical characteristic to be measured.

[17] The inspection method of the particulate matter detection device according to any one of [10] to [16], instead of the step of measuring the initial capacitance, further comprising the steps of: beforehand setting an initial electrical characteristic suitable for a constitution of the particulate matter detection device; and comparing a value of the set initial electrical characteristic with a value of the measured electrical characteristic, to inspect the particulate matter detection device for the abnormality.

[18] The inspection method of the particulate matter detection device according to any one of [10] to [17], which uses the particulate matter detection device further comprising: a unidirectionally long detection device main body having one end portion provided with at least one through hole; and the electrode portion including at least a pair of measurement electrodes disposed in the inner side surface or inside of one wall of the through hole, and at least a pair of dust collecting electrodes embedded in facing walls of the through hole, respectively, and outside a position of the wall of the through hole, where the pair of measurement electrodes are embedded, and covered with the dielectric material.

[19] The inspection method of the particulate matter detection device according to [18], further comprising the steps of comparing a value of the initial electrical characteristic with a value of the measured electrical characteristic, to inspect the device for at least one abnormality selected from the group consisting of disconnection, contact defect and break-down of the measurement electrode, short circuit of the pair of measurement electrodes and break-down of the dielectric material.

The particulate matter detection device of the present invention can judge whether or not the detection of the particulate matter is normally performed and satisfactorily inspect the device for break-down or defect. Moreover, the inspection method of the particulate matter detection device of the present invention can judge whether or not the detection of the particulate matter is normally performed and satisfactorily inspect the device for break-down or defect in the particulate matter detection device comprising the electrode portion which detects the particulate matter in the exhaust gas.

That is, according to the particulate matter detection device and the inspection method of the particulate matter detection device of the present invention, it is possible to compare the initial electrical characteristic in the use initial state with the electrical characteristic measured in the state where the particulate matter attached to the particulate matter detection device which is being used is removed, thereby judging (inspecting) whether or not the particulate matter detection device has the abnormality. For example, the electrode portion originally has a capacitance (an electrical characteristic). In a case where the capacitance is used as the initial capacitance, it is possible to detect a capacitance which is to become substantially equal to the initial capacitance when the removal means removes the particulate matter from the electrode portion. Therefore, both the characteristics (the initial electrical characteristic and the measured electrical characteristic) can be compared to judge whether or not the particulate matter detection device has the abnormality. For example, when both the characteristics have different values, it can be judged that the device is defective (abnormal).

The particulate matter detection device of the present invention can confirm whether or not normal measurement is performed at the present moment in the detection device which does not receive any signal concerning the detection or the detection device which receives a remarkably small signal indicating 'non-detected' if the signal is received and which recognizes that the signal is first detected if the signal is detected, for example, in a case where an exhaust gas treatment device normally functions. Therefore, it is possible to simply confirm a zero point of the particulate matter detection device and also confirm a defect (an abnormality) such as the break-down of the detection device.

Moreover, in the particulate matter detection device and the inspection method of the particulate matter detection device of the present invention, it is possible to limit or specify a place where the defect has occurred or contents of the defect in accordance with an obtained electrical characteristic value. Therefore, when the defect occurs, it is possible to simply and readily perform an operation such as replacement or repair of a defective portion.

It is to be noted that, for example, in a case where the particulate matter detection device comprises at least a pair of dust collecting electrodes embedded in the wall of the through hole of the detection device main body and can electrically adsorb the charged particulate matter by the measurement electrodes disposed in the wall face of the through hole or the inner surface of this wall, it is possible to measure the change of the electrical characteristic of the wall of the through hole by the pair of measurement electrodes disposed to face each other, thereby satisfactorily measuring the mass of the particulate matter in the exhaust gas which has flowed into the through hole among the exhaust gas flowing through the DPF on the downstream side thereof.

It is to be noted that the above particulate matter detection device does not directly measure all the particulate matter contained in the exhaust gas flowing through the DPF on the downstream side thereof, but measures the particulate matter which has flowed into the through hole, whereby the amount of the particulate matter in the whole exhaust gas can approximately be estimated on the basis of the measured value. In consequence, the micro amount of the particulate matter can be measured.

DESCRIPTION OF THE PREFERRED EMBODIMENT

Next, an embodiment of the present invention will be described in detail with reference to the drawings, but it should be understood that the present invention is not limited to the following embodiment but can appropriately be subjected to design change, modification or the like based on ordinary knowledge of a person with ordinary skill without departing from the scope of the present invention.

Figure 1A:
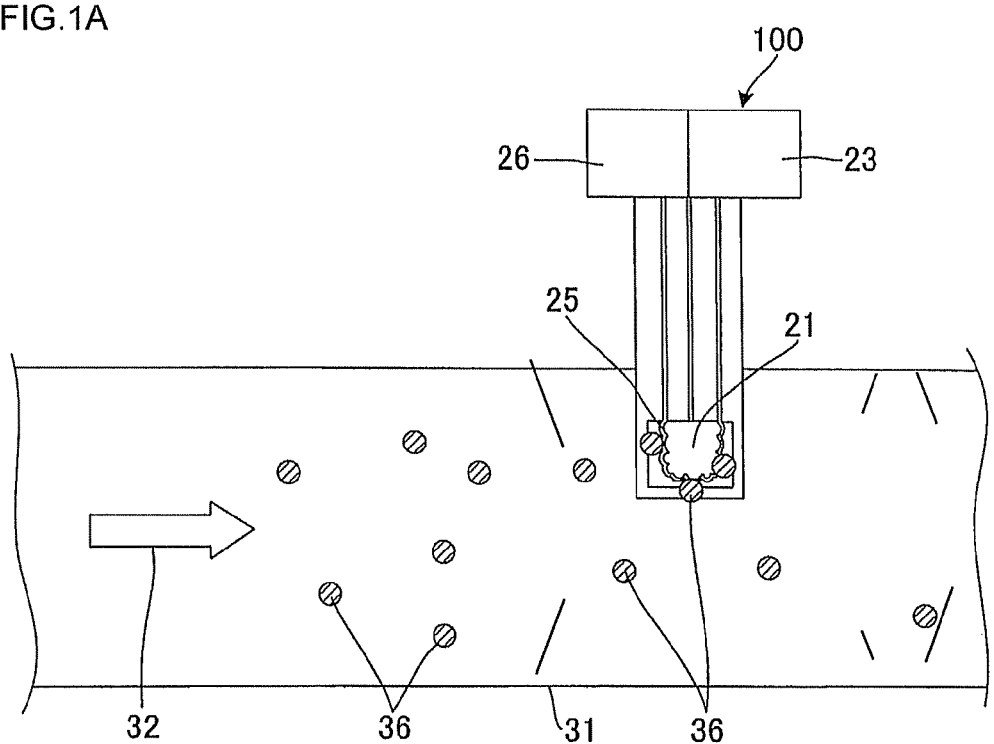
FIG. 1A is an explanatory view schematically showing one embodiment of a particulate matter detection device of the present invention.
Figure 1B:
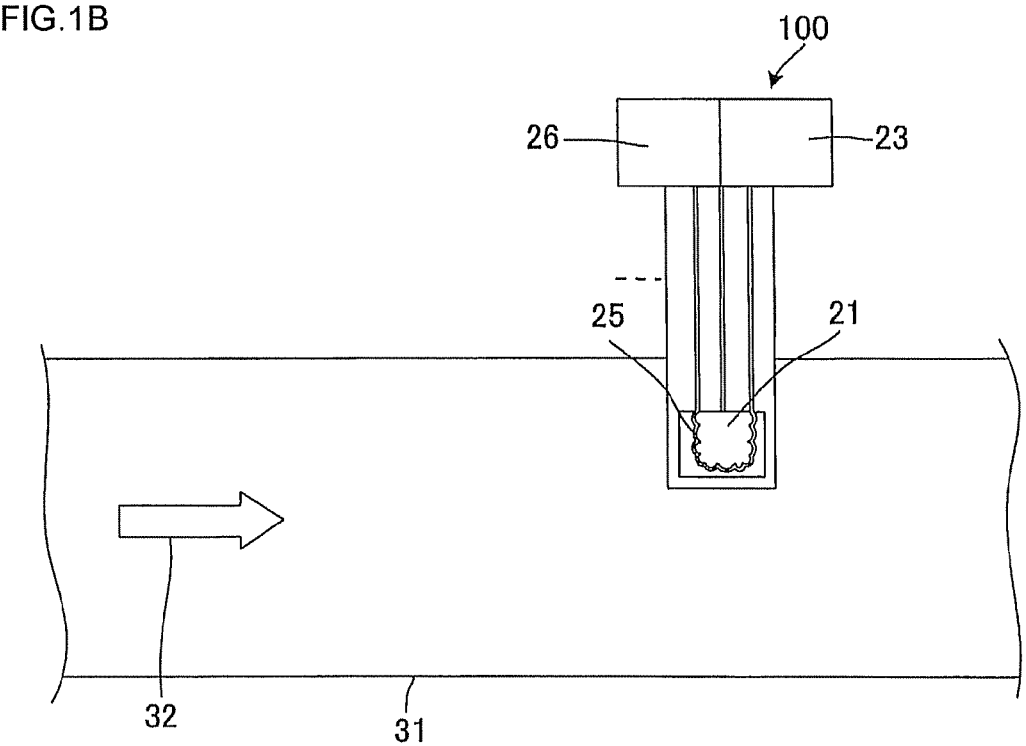
FIG. 1B is an explanatory view schematically showing one embodiment of the particulate matter detection device of the present invention.

[1] Characteristics of Particulate Matter Detection Device of the Present Invention:

FIG. 1A and FIG. 1B are explanatory views schematically showing one embodiment of a particulate matter detection device of the present invention. It is to be noted that FIG. 1A shows a state where a particulate matter is attached to an electrode portion of the particulate matter detection device, and FIG. 1B shows a state where any particulate matter is not attached to the electrode portion of the particulate matter detection device (the particulate matter has been removed).

As shown in FIGS. 1A and 1B, a particulate matter detection device 100 of the present embodiment comprises an electrode portion 21 disposed in an exhaust system 31 of an internal combustion engine 30, and detection means 23 for detecting an electrical characteristic of the electrode portion 21, whereby a particulate matter 36 contained in an exhaust gas 32 passing through the exhaust system 31 is detected on the basis of a change of the electrical characteristic due to the particulate matter 36 attached to the electrode portion 21. The particulate matter detection device 100 further comprises removal means 25 for removing the particulate matter 36 attached to the electrode portion 21; and abnormality judgment means 26 for measuring the electrical characteristic of the electrode portion 21 in a use initial state where any particulate matter 36 is not attached to the electrode portion 21, to obtain the electrical characteristic as an initial electrical characteristic, measuring the electrical characteristic of the electrode portion 21 in a state where the particulate matter 36 attached to the surface of the electrode portion 21 is removed by the removal means 25 to start the detection of the particulate matter by the particulate matter detection device 100 as shown in FIG. 1B, and comparing a value of the measured electrical characteristic with a value of the initial electrical characteristic to judge whether or not the particulate matter detection device 100 has an abnormality.

That is, the particulate matter detection device of the present embodiment comprises an abnormality judgment mechanism which measures the electrical characteristic of the electrode portion for detecting the particulate matter in the use initial state where any particulate matter is not attached to the particulate matter detection device and in the state where the particulate matter attached to the surface of the particulate matter detection device which is being used is removed to start the detection of the particulate matter by the particulate matter detection device, to judge, from these electrical characteristic values, whether or not the device has the abnormality.

According to such a constitution, the device can judge whether or not the detection of the particulate matter is normally performed and satisfactorily inspect the device for break-down or defect. For example, the electrode portion originally has a capacitance (the electrical characteristic). In a case where the capacitance is used as an initial capacitance, it is possible to detect a capacitance which is to become substantially equal to the initial capacitance when the removal means removes the particulate matter from the electrode portion. Therefore, both the electrical characteristics (the initial electrical characteristic and the measured electrical characteristic) can be compared to judge whether or not the particulate matter detection device has the abnormality. For example, when both the characteristics have different values, it can be judged that the device is defective (abnormal).

The particulate matter detection device of the present embodiment can confirm whether or not normal measurement is performed at the present moment in the detection device which does not receive any signal concerning the detection or the detection device which receives a remarkably small signal indicating 'non-detected' if the signal is received and which recognizes that the signal is first detected if the signal is detected, for example, in a case where an exhaust gas treatment device normally functions. Therefore, it is possible to simply confirm a zero point of the particulate matter detection device and also confirm a defect (an abnormality) such as the break-down of the detection device.

Moreover, the particulate matter detection device of the present embodiment can limit or specify a place where the defect has occurred or contents of the defect in accordance with an obtained electrical characteristic value. Therefore, when the defect occurs, it is possible to simply and readily perform an operation such as replacement or repair of a defective portion.

It is to be noted that in the present invention, 'the abnormality' include various defects occurring in the particulate matter detection device. In particular, the abnormality is a state where during the detection of the particulate matter, a change which originally does not occur is caused in the electrical characteristic of the electrode portion to disturb normal measurement. As described above, in the particulate matter detection device of the present invention, the change of the device which does not change the electrical characteristic to be detected (measured) by the electrode portion is not recognized as 'the abnormality'. The abnormality which does not change the electrical characteristic does not influence the detection of the particulate matter, and does not obstruct the normal detection of the particulate matter (e.g., simple color change which does not involve any change of the electrical characteristic).

The electrode portion attaches the particulate matter thereto, and measures the change of the electrical characteristic caused by the attached particulate matter. That is, the electrode portion is an electrode for use as a detecting portion (a sensor) of the particulate matter detection device. Examples of such an electrode of the electrode portion include an electrode formed by coating the surface of the device or the like with a conductive paste, and an electrode made of a metal plate or the like. This electrode portion is electrically connected to the detection means, so that the electrical characteristic of the electrode portion can be detected (measured) by the detection means.

Moreover, in addition to the electrode for measuring the particulate matter, the electrode portion may include an electrode for generating an electric field to collect dust, i.e., the particulate matter contained in the exhaust gas in the device. That is, in the particulate matter detection device of the present embodiment, the particulate matter in the exhaust gas is attached to the particulate matter detection device (especially, the electrode portion), and the change of the electrical characteristic of the electrode (hereinafter referred to as 'the measurement electrode' sometimes) constituting the electrode portion is read to detect the particulate matter in the exhaust gas from the change of the electrical characteristic. Therefore, the device may further comprise an electrode (hereinafter referred to as 'the dust collecting electrode' sometimes) for generating the electric field around the particulate matter detection device to collect the particulate matter flowing through the exhaust gas.

The detection means reads the change of the electrical characteristic to be measured by the electrode portion to detect the particulate matter contained in the exhaust gas in accordance with the electrode portion and the particulate matter attached to the periphery of the electrode portion. The greater part of the particulate matter contained in the exhaust gas is soot, and hence the particulate matter has conductivity. When the particulate matter is attached to the electrode portion or the like, the electrical characteristic to be measured changes. Therefore, the change of the electrical characteristic of the electrode portion disposed in the exhaust system of the internal combustion engine can be measured to detect whether or not the particulate matter is contained in the exhaust gas.

Examples of specific detection means include a detecting portion (a detection circuit) which detects the particulate matter contained in the exhaust gas from the change of the electrical characteristic of the electrode portion. For example, in a method, in a case where the electrical characteristic of the electrode portion to be measured is a capacitance, when an AC voltage is applied to one electrode and the capacitance changes, the voltage is detected as a voltage which is proportional to the capacitance by a converter or a charge amplifier connected to the other electrode, thereby inspecting (judging) the device for the abnormality in accordance with the change. It is to be noted that the present invention is not limited to the above inspection method, as long as the change of the electrical characteristic can be detected.

It is to be noted that as a constitution of a particulate matter detecting portion of the particulate matter detection device, a constitution of a detecting portion of a heretofore known particulate matter detection device may be employed. Examples of such a particulate matter detection device include a particulate matter detection device disclosed in JP-A-2009-186278.

The removal means removes the particulate matter attached to the electrode portion. In the particulate matter detection device of the present embodiment, this removal means removes the particulate matter attached to the electrode portion to obtain such a state as to start the detection of the particulate matter by the particulate matter detection device (hereinafter referred to as 'the detection start state' sometimes). In consequence, the device measures the electrical characteristic of the electrode portion, and compares the measured electrical characteristic with the initial electrical characteristic to judge whether or not the device has the abnormality.

As described above, when the particulate matter contained in the exhaust gas has the conductivity and the particulate matter is attached to the electrode portion or the like, the electrical characteristic to be measured changes. Therefore, in a case where the abnormality judgment is performed, when the particulate matter is still attached to the electrode portion, it cannot be judged whether the change of the electrical characteristic is caused by the attached particulate matter or the abnormality of the device, and accurate abnormality judgment cannot be performed.

Therefore, when the particulate matter detection device does not comprise any removal means and the device cannot be recovered to the detection start state, a value cannot strictly be compared with an initial value (the initial electrical characteristic), and it cannot accurately be judged whether or not the device has the abnormality. That is, only when the particulate matter detection device of the present embodiment comprises both the removal means and the abnormality judgment means, accurate abnormality judgment can be performed.

In this way, the particulate matter detection device of the present invention comprises constitutions: (1) the device comprises the removal means for removing the particulate matter attached to the electrode portion; (2) the device measures the electrical characteristic of the electrode portion after removing the particulate matter attached to the electrode portion by the removal means; and (3) the device obtains, as the initial electrical characteristic, the electrical characteristic measured in the use initial state where any particulate matter is not attached to the electrode portion, whereby it is possible to perform remarkably accurate abnormality judgment. For example, when the device does not comprise even one of the above constitutions, during the abnormality judgment, the accurate abnormality judgment cannot be performed.

It is to be noted that the above removal means can preferably remove not only the particulate matter attached to the electrode portion but also a particulate matter attached to another portion of the device, for example, the periphery of the electrode portion or the like.

For example, in the particulate matter detection device, the particulate matter is attached to a portion other than the electrode portion sometimes, and the electrical characteristic to be measured by the electrode portion is influenced by the attached particulate matter sometimes. Therefore, the removal means is preferably configured to remove, from the particulate matter detection device, all the particulate matters attached to the portions which influence the electrical characteristic to be measured.

There is not any special restriction on the constitution of the removal means as long as the particulate matter attached to the electrode portion, more preferably, the particulate matter detection device can be removed, but examples of the removal means include a heater which can apply heat to a portion which changes the electrical characteristic to be measured by the electrode portion to burn and remove the attached particulate matter. FIG. 1A and FIG. 1B show an example in which the device comprises the removal means including the heater. It is to be noted that such removing of the particulate matter attached to the electrode portion by the removal means will hereinafter be referred to as 'regeneration' of the particulate matter detection device sometimes.

The abnormality judgment means compares the initial electrical characteristic with the electrical characteristic measured after the regeneration to detect various abnormalities in the device. Examples of the means include an integrated circuit which calculates a difference (a change amount) between the initial electrical characteristic and the electrical characteristic measured after the regeneration to judge, from this change amount, whether or not the device has the abnormality. For example, in this integrated circuit, the type (the stereotype) of the expected abnormality is set in accordance with a size of the change amount of the electrical characteristic or an absolute value of the electrical characteristic measured after the regeneration, and the type corresponding to the above change amount or the like is selected to perform the abnormality judgment.

It is to be noted that 'the use initial state where any particulate matter is not attached to the particulate matter detection device' for measuring the initial electrical characteristic is, for example, a state where a manufactured particulate matter detection device is not used yet, or a state where the particulate matter is detected, but the particulate matter attached to the particulate matter detection device is removed, and it is revealed that the particulate matter detection device normally functions. That is, this initial electrical characteristic is an electrical characteristic as a reference in a case where it is judged whether or not the particulate matter detection device has the abnormality, an electrical characteristic in a case where the device is not used and has a normal state (i.e., the state where the device does not have any abnormality), or an electrical characteristic in a case where the device is used but is regenerated to recover a state similar to the unused state, and has the normal state.

For example, as to the initial electrical characteristic, the electrical characteristic is measured in a state where the particulate matter detection device is first used, and the measured value may be stored as the initial electrical characteristic in the abnormality judgment means. Alternatively, for example, when a large amount of particulate matter detection devices having the same constitution are manufactured, and the particulate matter detection devices are installed and used in various cars and the like, a unified initial electrical characteristic may beforehand be set to the particulate matter detection devices having the same constitution. That is, when the value of the initial electrical characteristic is beforehand known in a specific particulate matter detection device, a step of measuring the initial electrical characteristic may be omitted, and the set initial electrical characteristic may be compared with the electrical characteristic measured after the regeneration to inspect the device for the abnormality.

As described above, as to the particulate matter detection device of the present embodiment, when the device has the abnormality, the electrical characteristic to be measured by the electrode portion changes, and hence the abnormality can be detected. Furthermore, it is possible to limit or specify the type or place of the abnormality in accordance with a difference (i.e., the change amount) between the initial electrical characteristic and the electrical characteristic after the regeneration, or the value (i.e., the absolute value) of the electrical characteristic after the regeneration.

When a specific abnormality is, for example, disconnection or contact defect of the electrode constituting the electrode portion, after the regeneration, the electrical characteristic having a value to be measured by the electrode portion is not measured, and the initial electrical characteristic becomes different from the electrical characteristic after the regeneration. For example, when the disconnection of the electrode or the like occurs just near the detecting portion for measuring the electrical characteristic and the electrical characteristic is a resistance, the resistance after the regeneration becomes remarkably large (e.g., 100 MΩ or more). Alternatively, when the electrical characteristic is the capacitance (unit: pF), the capacitance is 0 pF.

Moreover, when the electrical characteristic to be compared by the abnormality judgment means is the capacitance, the initial capacitance as the initial electrical characteristic is compared with the value of the measured capacitance (the electrical characteristic after the regeneration) and a difference between the capacitances is 0.5 pF or more, it can then be judged, depending on the constitution of the particulate matter detection device, that the device has at least one abnormality selected from the group consisting of break-down of the electrode portion, short circuit of a pair of electrode portions when the electrode portion comprises a pair of electrode portions, and break-down of the dielectric material when at least a part of the electrode portion is covered with the dielectric material. It is to be noted that such an abnormality judgment standard is merely one example, and an optimum judgment standard is set in accordance with the constitution of each portion of the particulate matter detection device. There is not any special restriction on the judgment standard as long as the particulate matter detection device of the present invention can compare the electrical characteristic measured after removing the particulate matter by the removal means with the initial electrical characteristic to perform the abnormality judgment by the abnormality judgment means.

Figure 2:
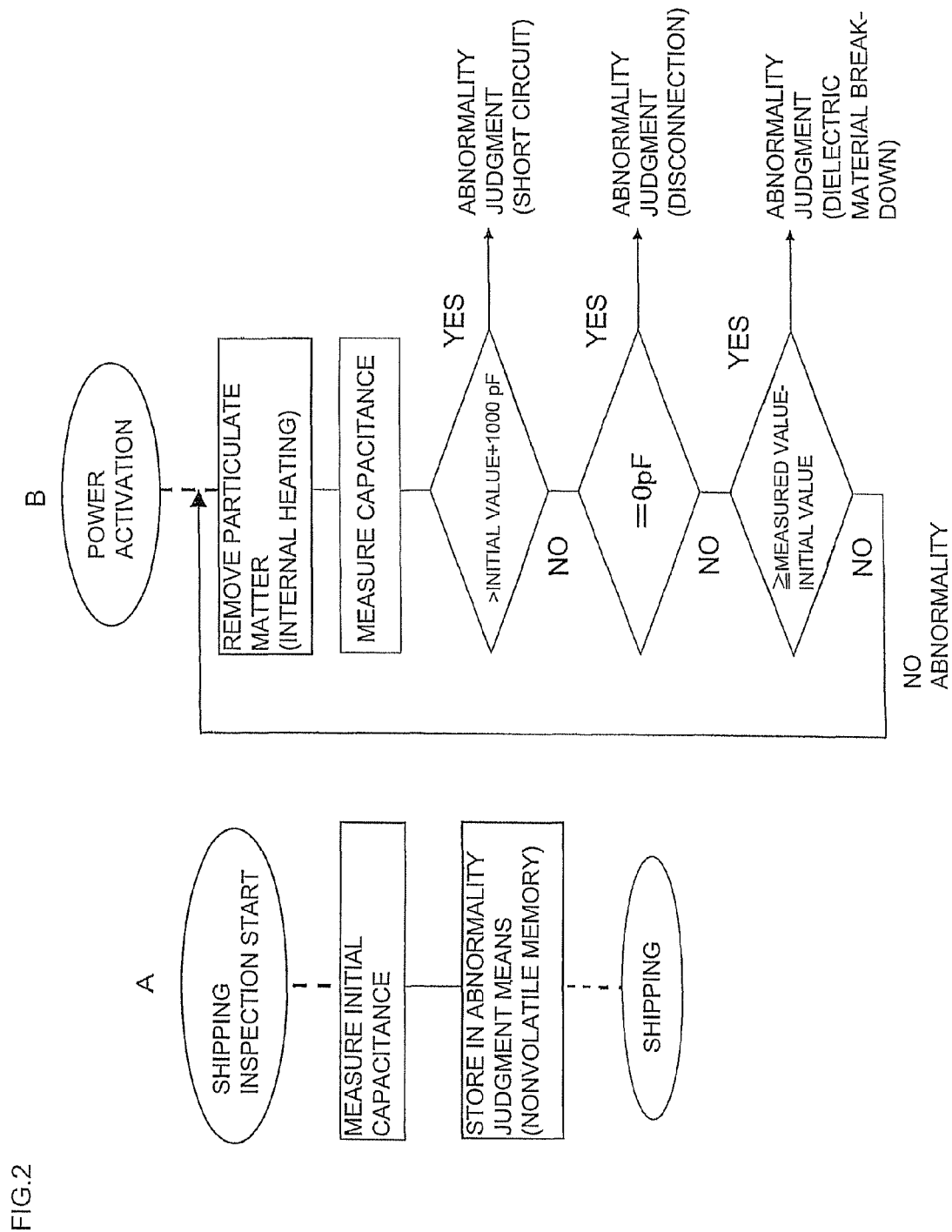
FIG. 2 is a flowchart showing one example of an abnormality judgment method in the particulate matter detection device of the present invention.

Here, one example of an abnormality judgment method in the particulate matter detection device of the present embodiment will be described with reference to a flowchart shown in FIG. 2. The flowchart shown in FIG. 2 shows the abnormality judgment method using the capacitance as the electrical characteristic. Furthermore, this flowchart shows two steps, i.e., a step (step A) of measuring the initial capacitance and a step (step B) of measuring the capacitance after removing the particulate matter to actually perform the abnormality judgment.

First, the step A measures the initial capacitance in a shipping inspection. The measured initial capacitance is stored in a nonvolatile memory disposed in the abnormality judgment means. In the subsequent abnormality judgment, the initial capacitance stored in this nonvolatile memory is compared with the capacitance measured after removing the particulate matter to perform the abnormality judgment. That is, the initial capacitance is measured once in this shipping inspection.

Next, in the step B, first, the particulate matter detection device is installed in a car or the like for use in the actual detection of the particulate matter (power activation). In this stage, the particulate matter detection device collects the particulate matter in the exhaust gas to detect the particulate matter, and detects the particulate matter from the change of the electrical characteristic of the electrode portion.

Next, when the abnormality judgment means performs the abnormality judgment, the removal means removes the particulate matter. In the flowchart shown in FIG. 2, the removal means heats the inside of the device to burn and remove the particulate matter attached to the electrode portion. Next, the abnormality judgment means measures the capacitance of the electrode portion. Subsequently, the means compares the measured capacitance with the initial capacitance stored in the abnormality judgment means (the nonvolatile memory) to perform the abnormality judgment.

First, when the measured capacitance is 1000 pF larger than the initial value (the initial capacitance) (>the initial value+1000 pF), it is judged that the abnormality is the short circuit of the electrode portion. It is to be noted that when the capacitance is less than 1000 pF, the next abnormality judgment is performed. In the next abnormality judgment, it is judged whether or not the measured capacitance is 0 pF. When the capacitance is 0 pF, it is judged that the abnormality is the disconnection of the electrode portion (the disconnection just near the detecting portion). It is to be noted that when the measured capacitance is not 0 pF, the next abnormality judgment is performed.

In the next abnormality judgment, the measured capacitance value is compared with the value of the initial capacitance to judge whether or not the abnormality is the break-down of the dielectric material, in accordance with a difference between the capacitance values (i.e., 'the measured capacitance value'–'the value of the initial capacitance', i.e., 'the measured value–the initial value' in the flowchart). When the difference between the initial capacitance value and the above measured capacitance value is 0.5 pF or more, it is judged that the abnormality is the break-down of the dielectric material. It is to be noted that in the above three or more judgments, when any abnormality is not judged (i.e., all answers to the judgments are 'no'), it is judged that the device does not have any abnormality. It is to be noted that when it is judged that the device does not have any abnormality, the abnormality judgment may be ended at this time, or a further abnormality judgment may be performed with respect to another electrode constituting the electrode portion.

It is to be noted that there is not any special restriction on the particulate matter detection device of the present embodiment, but preferably in the particulate matter detection device, the electrical characteristic to be compared by the abnormality judgment means is the capacitance, and the initial capacitance as the initial electrical characteristic is set to a range of 0 to 100 pF. In such a particulate matter detection device, it has heretofore been remarkably difficult to perform the abnormality judgment, but when the device is configured to perform the above abnormality judgment, accurate abnormality judgment can be performed.

It is to be noted that the electrical characteristic for detecting the particulate matter (i.e., the electrical characteristic measured by the detection means) and the electrical characteristic for judging whether or not the device has the abnormality (i.e., the electrical characteristic measured after the regeneration) may be the same type of electrical characteristic or different types of electrical characteristics. For example, the detection of the particulate matter may be performed in accordance with the capacitance, and the abnormality judgment may be performed in accordance with the resistance. Alternatively, both the detection of the particulate matter and the abnormality judgment may be performed in accordance with, for example, the capacitance. When the same electrical characteristic is used, a detector of the particulate matter detection device may also be used for the abnormality judgment, which can simplify the constitution of the device. Moreover, as described above, the type of the electrical characteristic may separately be selected in accordance with the contents of abnormality detection (judgment) or the like.

Moreover, in the particulate matter detection device of the present embodiment, at least a part of the electrode portion is covered with the dielectric material, and the above abnormality judgment means measures the electrical characteristic of the electrode portion while raising the temperature of the dielectric material, to further inspect the device for the disconnection or contact defect of the electrode portion or the break-down of the dielectric material from the change of the electrical characteristic to be measured.

That is, in the particulate matter detection device of the present embodiment, at least a part of the electrode portion is covered with the dielectric material as described above. When the particulate matter is attached to the dielectric material, the device may measure the electrical characteristic of the electrode portion to detect the particulate matter. In this case, the device measures the electrical characteristic of the electrode portion while raising the temperature of the dielectric material, which enables further detailed abnormality judgment.

When the dielectric material is heated, the resistance thereof lowers, and the electrical characteristic to be measured by the electrode portion changes with the temperature change of the dielectric material. However, when the abnormality occurs in the particulate matter detection device, the obtained electrical characteristic indicates a characteristic behavior in accordance with the occurring defect (the abnormality) sometimes.

When the temperature of the dielectric material is raised, a temperature raising rate is, for example, preferably from 5 to 50° C./second, further preferably from 10 to 40° C./second, especially preferably from 15 to 35° C./second. When the temperature raising rate is, for example, less than 5° C./second and inspection is performed in a broad temperature range, inspection time unfavorably lengthens. On the other hand, when the temperature raising rate exceeds 50° C./second, the temperature raising rate is so high that the characteristic behavior due to the defect is missed sometimes. Moreover, when the temperature raising rate is excessively high, the particulate matter detection device might break down owing to thermal shock.

For example, in a case where the electrode portion is disconnected, even when the temperature of the dielectric material rises, the measured electrical characteristic (e.g., the capacitance or the resistance) does not change, and indicates a constant value regardless of the temperature change. Moreover, for example, when the dielectric material has cracks (micro cracks or the like), the dielectric material expands, a gap between the micro cracks increases, and the electrical characteristic to be measured rises excessively as compared with the temperature rise. In consequence, more accurate abnormality judgment can be performed.

It is to be noted that when such abnormality judgment is performed, response of a detection circuit of the abnormality judgment means is preferably 10 Hz or more. When the response of the detection circuit is, for example, less than 10 Hz and the abnormality occurs, the characteristic behavior occurring in accordance with each defect (abnormality) is missed sometimes.

When the temperature of the dielectric material is raised and the particulate matter detection device comprises, for example, a heating portion (e.g., the heater), the temperature may be raised by using the heating portion, or the dielectric material may be heated by radiant heat from a heat source disposed outside the particulate matter detection device. It is to be noted that when the removal means of the particulate matter detection device comprises a heater, the dielectric material may be heated by using the heater.

Moreover, when the dielectric material is heated in this manner, the whole dielectric material is not evenly heated, but, for example, the dielectric material may partially be heated. For example, when the dielectric material which covers the electrode portion is a unidirectionally long detection device main body (hereinafter referred to as 'the detection device main body' sometimes), one end portion or the other end portion of the detection device main body or one side surface thereof in a longitudinal direction may only be heated, thereby measuring the change of the electrical characteristic with the temperature change. For example, when the dielectric material has cracks, a part of the dielectric material may be heated and thermally expanded as described above, whereby the gap between cracks such as micro cracks can temporarily be increased. In consequence, the change of the measured electrical characteristic becomes remarkable, which enables more detailed abnormality judgment.

Furthermore, in the particulate matter detection device of the present embodiment, at least a part of the electrode portion is covered with the dielectric material, and during the measurement of the electrical characteristic of this electrode portion, the device is configured to measure the electrical characteristic while changing the frequency of the voltage to be applied to the electrode portion. The device may be configured to inspect the dielectric material for the break-down in accordance with transition of the measured electrical characteristic.

For example, when the dielectric material has cracks (the micro cracks or the like), the value of the electrical characteristic (e.g., the capacitance or the resistance) noticeably changes at a specific frequency sometimes. This is because when the dielectric material has a piezoelectric effect, a mechanical resonance phenomenon occurs in accordance with a micro crack dimension owing to electromechanical transform, and an apparent electrical characteristic (e.g., the capacitance) noticeably changes. In consequence, the abnormality judgment can more accurately be performed.

It is to be noted that in case of the changing of the frequency, the frequency is changed in a range, for example, preferably from 100 to 100M Hz, further preferably from 100 to 10M Hz, especially preferably from 1 k to 1 MHz. When the frequency changing range is smaller than the above range, it sometimes becomes difficult to find the micro cracks of the dielectric material. Moreover, from a practical viewpoint, the frequency is preferably set to 10 seconds/dec at longest.

When the particulate matter detection device of the present embodiment is installed and used in the exhaust system of the internal combustion engine, the above removal means preferably periodically regenerates the device, and with this regeneration of the device (i.e., after regenerating the device), the abnormality judgment means preferably performs the abnormality judgment. In consequence, the device can periodically be diagnosed, and the device abnormality can be found early. It is to be noted that in this case, as described above, the measurement of the initial electrical characteristic is omitted, and the abnormality judgment is performed by using the preset value of the initial electrical characteristic.

Moreover, when the particulate matter detection device is installed and used in the exhaust system of the car, at the start of an engine of a car, the abnormality judgment means may constantly perform the abnormality judgment. In this way, the start of the engine of the car and the abnormality judgment are cooperatively performed, whereby when the abnormality occurs in the particulate matter detection device, the abnormality can be found earlier.

Figure 3A:
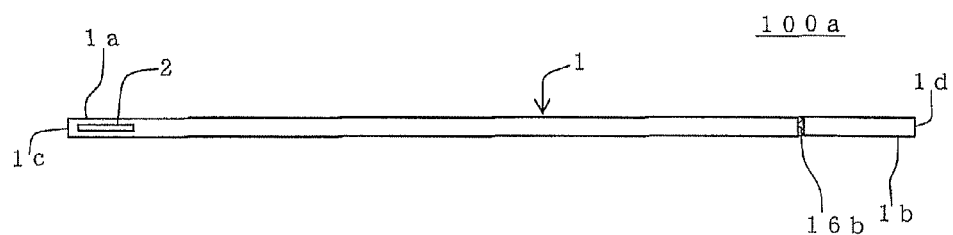
FIG. 3A is a front view schematically showing a particulate matter detection device which is an inspection target in one embodiment of an inspection method of the particulate matter detection device of the present invention.
Figure 3B:
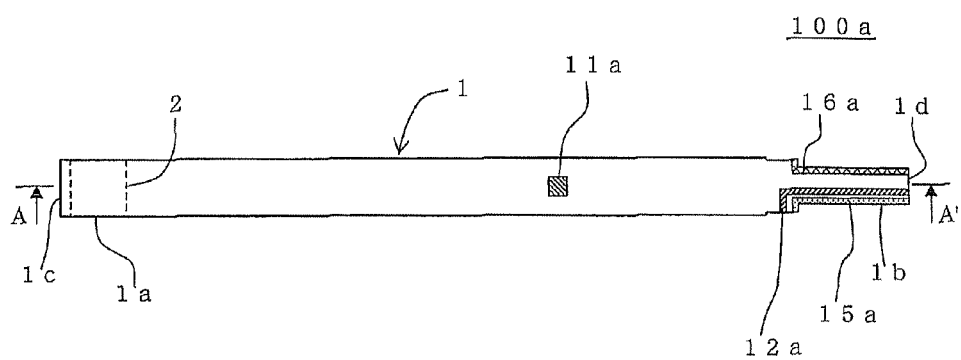
FIG. 3B is a side view showing one side surface of the particulate matter detection device shown in FIG. 3A.
Figure 3C:
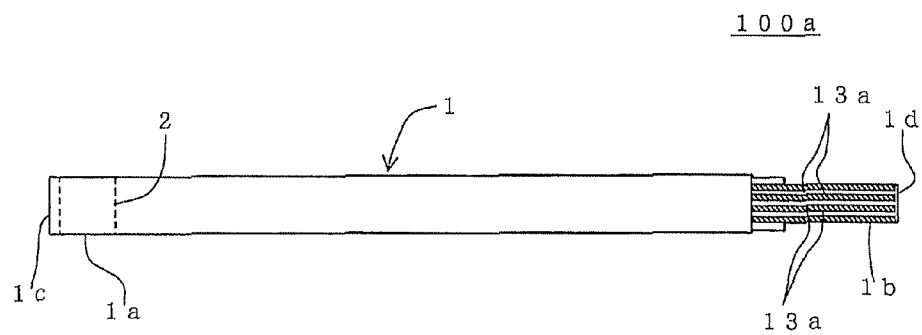
FIG. 3C is a side view showing the other side surface of the particulate matter detection device shown in FIG. 3A.
Figure 3D:
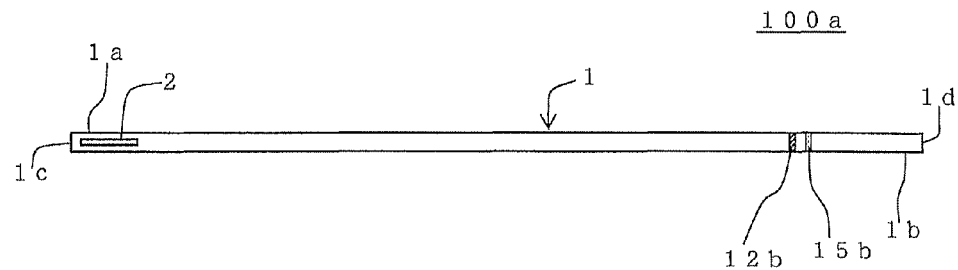
FIG. 3D is a back view of the particulate matter detection device shown in FIG. 3A.
Figure 4:
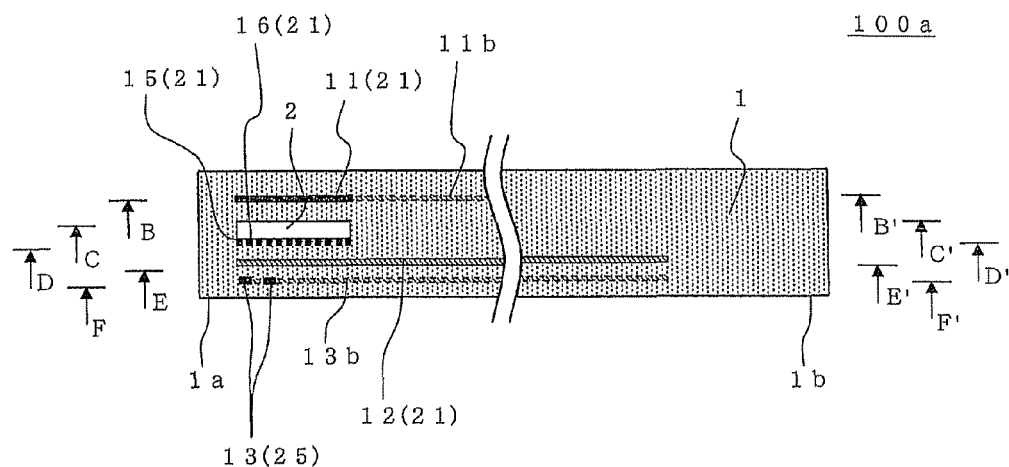
FIG. 4 is an exemplary diagram showing a section cut along the A-A' line of FIG. 3B.
Figure 5:
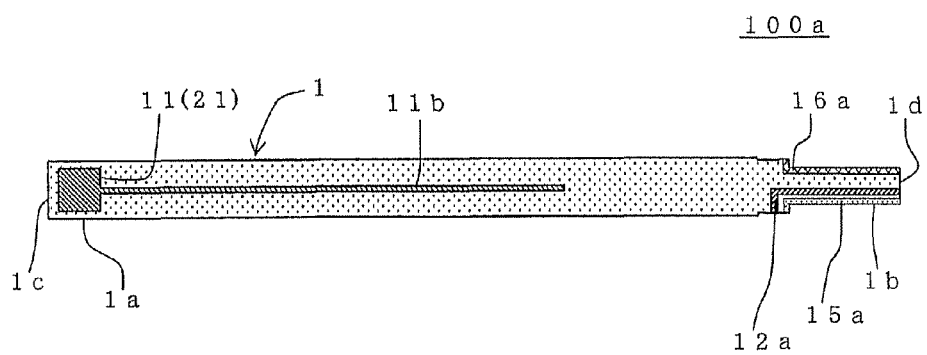
FIG. 5 is an exemplary diagram showing a section cut along the B-B' line of FIG. 4.
Figure 6:
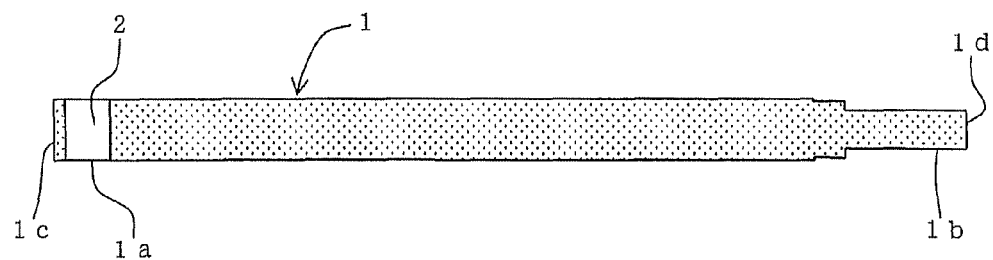
FIG. 6 is an exemplary diagram showing a section cut along the C-C' line of FIG. 4.
Figure 7:
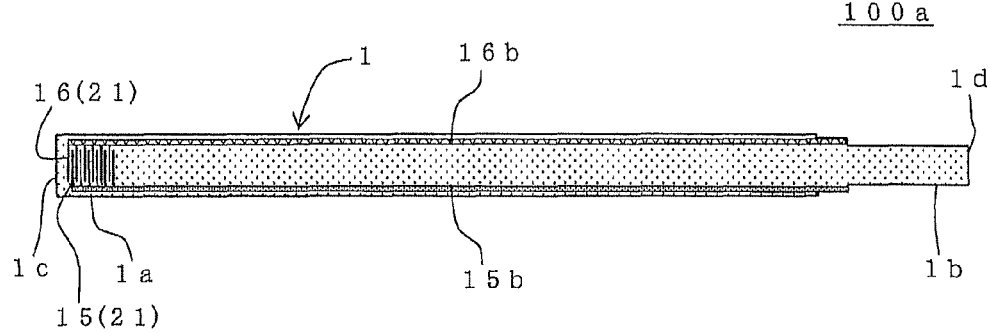
FIG. 7 is an exemplary diagram showing a section cut along the D-D' line of FIG. 4.
Figure 8:
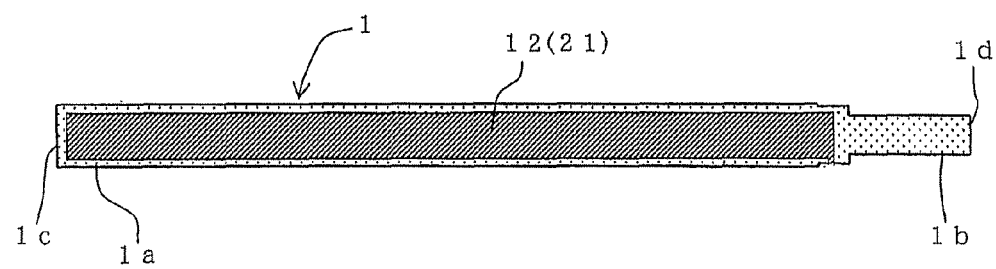
FIG. 8 is an exemplary diagram showing a section cut along the E-E' line of FIG. 4.
Figure 9:
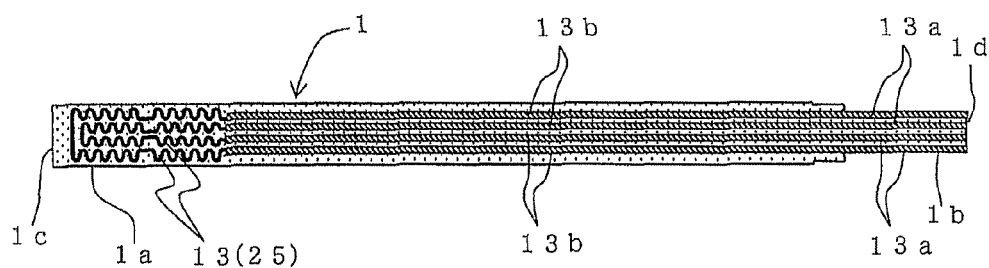
FIG. 9 is an exemplary diagram showing a section cut along the F-F' line of FIG. 4.

[2] Constitution of Particulate Matter Detection Device of the Present Invention:

Next, as to one embodiment of the particulate matter detection device of the present invention, an example of the particulate matter detection device will be described in further detail with reference to FIG. 3A to FIG. 3D and FIG. 4 to FIG. 9. Here, FIG. 3A is a front view schematically showing one embodiment of the particulate matter detection device of the present invention, FIG. 3B is a side view showing one side surface of the particulate matter detection device shown in FIG. 3A, FIG. 3C is a side view showing the other side surface of the particulate matter detection device shown in FIG. 3A, and FIG. 3D is a back view of the particulate matter detection device shown in FIG. 3A. Moreover, FIG. 4 is an exemplary diagram showing a section cut along the A-A' line of FIG. 3B, FIG. 5 is an exemplary diagram showing a section cut along the B-B' line of FIG. 4, FIG. 6 is an exemplary diagram showing a section cut along the C-C' line of FIG. 4, FIG. 7 is an exemplary diagram showing a section cut along the D-D' line of FIG. 4, FIG. 8 is an exemplary diagram showing a section cut along the E-E' line of FIG. 4, and FIG. 9 is an exemplary diagram showing a section cut along the F-F' line of FIG. 4.

A particulate matter detection device 100a shown in FIG. 3A to FIG. 3D and FIG. 4 to FIG. 9 comprises a unidirectionally long detection device main body 1 having one end portion 1a provided with at least one through hole (a cavity) 2; at least a pair of measurement electrodes 15 and 16 disposed in the inner side surface or inside of one wall of the through hole 2; and at least a pair of dust collecting electrodes 11 and 12 embedded in facing walls of the through hole 2, respectively, and outside a position of the wall of the through hole 2 where the pair of measurement electrodes 15 and 16 are embedded, and covered with a dielectric material. The particulate matter detection device 100a is configured to detect a particulate matter contained in an exhaust gas. The pair of measurement electrodes 15 and 16 and the pair of dust collecting electrodes 11 and 12 constitute the electrode portion 21 of the particulate matter detection device 100a. The pair of measurement electrodes 15 and 16 and the pair of dust collecting electrodes 11 and 12 are connected to leading terminals 15a, 16a, 11a and 12a via wiring lines 15b, 16b, 11b and 12b, and the leading terminals 15a, 16a, 11a and 12a are electrically connected to the detection means 23 (see FIG. 1A) and the abnormality judgment means 26 (see FIG. 1A). Moreover, the particulate matter detection device 100a comprises a heating portion 13 as the removal means 25.

This particulate matter detection device measures the electrical characteristic of the measurement electrodes 15 and 16 in a use initial state where any particulate matter is not attached to the measurement electrodes 15 and 16 to obtain the electrical characteristic as the initial electrical characteristic, and measures the electrical characteristic of the measurement electrodes 15 and 16 in a state where the particulate matter attached to the surfaces of the measurement electrodes 15 and 16 is removed by the heating portion 13 to start the detection of the particulate matter by the particulate matter detection device 100a. The device compares the a value of measured electrical characteristic with a value of the initial electrical characteristic by the abnormality judgment means 26 (see FIG. 1A) to judge whether or not the particulate matter detection device 100a has an abnormality.

In this way, for example, the device can be inspected for the disconnection or break-down of the measurement electrode, the short circuit of the pair of measurement electrodes, the break-down of the dielectric material or the like. Therefore, it can be judged whether or not the detection of the particulate matter is normally performed by the particulate matter detection device, and the device can satisfactorily be inspected for the break-down or a defect.

Examples of the electrical characteristic measured by such detection means and abnormality judgment means of the particulate matter detection device include a capacitance and a resistance.

For example, when the particulate matter detection device is inspected for the abnormality, to measure the capacitance as the electrical characteristic between the pair of measurement electrodes, an AC voltage is applied to one measurement electrode on conditions of, for example, 1 Vrms and 1 kHz, and the other measurement electrode is connected to a circuit which detects a current or a charge with a low input impedance, for example, an I/V converter or a charge amplifier, thereby detecting the voltage which is proportional to the capacitance between the electrodes. Furthermore, in the detecting portion (the abnormality judgment means), synchronous detection is preferably performed so that the influence of an external noise can be eliminated. Such a method enables measurement, for example, in a measurement range of 0 to 100 pF and with a resolution of about 0.1 pF. During the measurement of the capacitance between the pair of measurement electrodes, for example, LCR Meter 4263B (trade name) manufactured by Agilent Technologies Co., Ltd. may be used.

The inspection can be performed on the above conditions, to inspect the particulate matter detection device for a remarkably small abnormality (defect). When the abnormality occurs in the particulate matter detection device, the abnormality can be found early. For example, in a time constant circuit which utilizes a time constant due to the capacitance between the electrodes and a circuit resistance, it sometimes becomes difficult to find the break-down of the dielectric material or a small defect such as partial failure of the measurement electrode. When such a small defect is left as it is and the device is continuously used, the defect might be developed to a serious defect. The defect is preferably found early to immediately perform replacement or repair of a defective portion.

It is to be noted that when the value of the initial electrical characteristic (e.g., the initial capacitance) is compared with the value of the electrical characteristic after the regeneration (e.g., the capacitance after the regeneration) and a difference is found between the values, it is possible to limit or specify the place of the abnormality occurring in the particulate matter detection device in accordance with a size of the difference. For example, a judgment standard (an inspection standard) for performing the abnormality judgment is set with respect to the difference between the initial capacitance and the capacitance after the regeneration compared with each other as described above, or the value (the absolute value) of the measured capacitance, and the inspection is preferably performed in accordance with this judgment standard.

The above judgment standard differs with the constitution or performance of the particulate matter detection device (e.g., a detection range, a detection limit or the like of the particulate matter detection device). However, for example, when a device (the particulate matter detection device) installed in a rear stage of a diesel particulate filter (DPF) in an exhaust system of a diesel engine and configured to detect whether or not a particulate matter is contained in a gas discharged from this DPF is inspected, for example, the judgment standard may be disposed as follows.

When the value of the measured capacitance is, for example, 0 pF, it can be judged (inspected) that the measurement electrodes 15 and 16 of the particulate matter detection device 100*a* shown in FIG. 3A to FIG. 3D has the disconnection or the contact defect.

That is, at least a part of the detection device main body 1 of the particulate matter detection device 100*a* is constituted of the dielectric material, and a pair of measurement electrodes are disposed in the inner side wall or inside of the one wall of the through hole 2 of the detection device main body 1 with a predetermined space being left between the electrodes. Therefore, when the capacitance between the pair of measurement electrodes 15 and 16 is measured, the capacitance having a certain constant size is measured. If the capacitance between the pair of measurement electrodes 15 and 16 is measured and the value of the measured capacitance is 0 pF, it is presumed that at least one measurement electrode 15 or 16 in the pair of measurement electrodes 15 and 16 has an abnormality such as the disconnection or the contact defect. It is to be noted that the above 'the measurement electrodes are disconnected' includes not only a case where the measurement electrodes themselves are disconnected but also a case where wiring lines connected to the measurement electrodes, for example, the measurement electrode wiring lines 15*b* and 16*b* (see FIG. 5) are disconnected. Moreover, 'the contact defect of the measurement electrode' indicates not only a contact defect between the measurement electrode and the wiring line connected to the electrode but also a contact defect between the abnormality judgment means and all sections electrically connected to the measurement electrode. Examples of the above contact defect of the measurement electrode also include a contact defect between the wiring line connected to the measurement electrode and a connection terminal.

It is to be noted that when the wiring line connected to the measurement electrode is halfway disconnected, a weak capacitance is sometimes detected, depending on, for example, the position of the disconnection. When the value of the measured capacitance is, for example, 0 pF as described above, it can be judged that the electrode is completely disconnected. However, for example, when the capacitance obviously lowers below the initial capacitance, but a remarkably weak capacitance is detected, it becomes difficult to perform the abnormality judgment (i.e., the selection of the type) sometimes. Therefore, when the judgment of an abnormality such as the disconnection is performed, a threshold value is set to about 0.5 pF, and the capacitance is detected as a change more than the influence of disturbance or regeneration fluctuation, whereby it can satisfactorily be judged whether or not the device has the abnormality. It is to be noted that when the value of the capacitance is 0 pF as described above, the influence of the wiring line or the like is not detected, and hence there is doubt of the disconnection or contact defect of the wiring line around the detector which measures the electrical characteristic.

Moreover, the above 'regeneration fluctuation' is a slight influence exerted to the measured value due to a remaining particulate matter, because when the removal means removes the particulate matter, the particulate matter cannot completely be removed, and a remarkably micro amount of the particulate matter remains in the electrode portion sometimes. However, the influence of the disturbance or the regeneration fluctuation on the measured value is remarkably slight. Therefore, when the threshold value is set as described above, accurate abnormality judgment can be performed. When the value remarkably changes from the initial value (the initial electrical characteristic), any threshold value is not especially set, but the abnormality judgment can be performed.

Furthermore, the inspection differs with, for example, the constitution of the particulate matter detection device, but when the value of the initial capacitance is compared with the value of the measured capacitance and a difference between the values is 0.5 pF or more, it can be judged (inspected) that the device has at least one type of abnormality selected from the group consisting of the break-down of the measurement electrode, the short circuit of the pair of measurement electrodes and the break-down of the dielectric material.

When the capacitance between the pair of measurement electrodes is measured as described above, a certain constant size of capacitance is measured. However, when the value of the capacitance becomes larger than that of the initial capacitance, some abnormality might occur in the measurement electrode or the dielectric material.

Specifically, in case of the break-down of the measurement electrode, for example, when a part of the measurement electrode has a failure, the decrease of the capacitance is measured in accordance with a failure distance. In a case where the electrodes are arranged at an equal interval, when the failure occurs, for example, at a half distance, the capacitance of an approximate half of the initial value (the initial capacitance) is measured. The minimum value of the failure which can be detected from such a relation is limited to a distribution of the capacitance due to the external noise or the regeneration fluctuation.

Moreover, when the short circuit of the pair of measurement electrodes occurs, a remarkably large current or charge, which cannot be measured owing to usual attachment of the particulate matter, is measured in the measurement electrode in accordance with the impedance of the short circuit.

Furthermore, in case of the break-down of the dielectric material, for example, when the dielectric material has cracks or a part of the dielectric material fails, the capacitance decreases with the decrease of dielectric constant. When, for example, alumina is utilized as the dielectric material and the dielectric material entirely fails, the value decreases to 1/8.5 of the initial value, because alumina has a dielectric constant of 8.5.

The above abnormality characteristics are taken into consideration, the judgment standard by the abnormality judgment means is set, and the abnormality judgment is performed in accordance with the judgment standard, whereby more accurate abnormality judgment can be performed.

Moreover, also in such a particulate matter detection device, while raising the temperature of the dielectric material (specifically, the detection device main body) constituting the particulate matter detection device, the capacitance between the pair of measurement electrodes may be measured, and the device may be inspected for the disconnection of the measurement electrode, the break-down of the dielectric material or the like in accordance with the change of the measured capacitance. Moreover, when the capacitance between the pair of measurement electrodes may be measured, the capacitance may be measured while changing the frequency of the voltage to be applied across the pair of measurement electrodes, and the device may be inspected for the break-down of the dielectric material in accordance with the transition of the measured capacitance.

Furthermore, the initial capacitance is the capacitance measured in the use initial state where any particulate matter is not attached to the particulate matter detection device. However, when the particulate matter detection devices having the same constitution are manufactured in large quantities, the unified initial capacitance may beforehand be set. That is, for example, when the value of the initial capacitance is beforehand known, the step of measuring the initial capacitance is omitted, the initial capacitance is set to the abnormality judgment means, and the preset initial capacitance may be compared with the capacitance after the regeneration to perform the abnormality judgment. It is to be noted that there has been described above the example where the capacitance is employed as the electrical characteristic, but there is not any special restriction on the type of the electrical characteristic as long as it can be judged, in accordance with the electrical characteristic, whether or not the device has the abnormality. The electrical characteristic may be, for example, the resistance, a dielectric loss or the like.

[2-1] Each Constituent Element of Particulate Matter Detection Device:

Next, each constituent element of the particulate matter detection device shown in FIG. 3A to FIG. 3D and FIG. 4 to FIG. 9 will be described in more detail.

The particulate matter detection device 100a shown in FIG. 3A to FIG. 3D and FIG. 4 to FIG. 9 comprises the unidirectionally long detection device main body 1 having the one end portion 1a provided with at least one through hole (the cavity) 2; at least the pair of measurement electrodes 15 and 16 disposed in the inner side surface or inside of the one wall of the through hole 2; and at least the pair of dust collecting electrodes 11 and 12 embedded in the facing walls of the through hole 2, respectively, and outside the position of the wall of the through hole 2 where the pair of measurement electrodes 15 and 16 are embedded, and covered with the dielectric material. The pair of measurement electrodes 15 and 16 and the pair of dust collecting electrodes 11 and 12 constitute the electrode portion.

The particulate matter detection device 100a further comprises the pair of measurement electrode wiring lines 15b and 16b extending from the pair of measurement electrodes 15 and 16 to the other end portion 1b of the detection device main body 1, respectively, and the pair of measurement electrodes 15 and 16 are each branched into a plurality of portions (e.g., branched into comb-like portions as shown in FIG. 7), and have a plurality of facing portions.

Moreover, in the particulate matter detection device 100a, the charged particulate matter contained in a fluid flowing into the through hole 2 or the particulate matter contained in the fluid flowing into the through hole 2 and charged by applying the voltage across the pair of dust collecting electrodes 11 and 12 can electrically be adsorbed by the wall face of the through hole 2. Furthermore, the change of the electrical characteristic of the wall of the through hole 2 is measured by the pair of measurement electrodes 15 and 16, whereby it is possible to detect the mass of the particulate matter adsorbed by the wall face of the through hole 2. In consequence, the particulate matter detection device 100a of the present embodiment can detect the particulate matter contained in the exhaust gas passed through the through hole 2 or the like.

The particulate matter detection device 100a does not directly measure all the particulate matter contained in the exhaust gas flowing through the DPF on the downstream side thereof or the like, but measures the particulate matter flowing into the through hole 2, and approximately estimates the amount of the particulate matter in the whole exhaust gas based on this measured value. In consequence, it is possible to measure the micro amount of the particulate matter.

Moreover, since the particulate matter detection device 100a does not measure the whole amount of the exhaust gas as described above, the particulate matter detection device 100a can be miniaturized, and can be installed in a small space.

Furthermore, even when the whole flow rate of the exhaust gas flowing through the DPF on the downstream side thereof or the like is a high flow rate, an only part of the exhaust gas (i.e., the particulate matter contained in the exhaust gas) is introduced into the through hole 2, whereby the particulate matter in the through hole 2 can effectively be charged. The measured value having a less error can be obtained.

In addition, the detection device main body 1 is formed to be unidirectionally long, and has the one end portion 1a provided with the through hole 2, and the pair of dust collecting electrodes 11 and 12 and the pair of measurement electrodes 15 and 16 are disposed (embedded). Therefore, the through hole 2 and the respective electrodes (e.g., the dust collecting electrode 11 or the pair of measurement electrodes 15 and 16) are disposed in a piping line through which the high-temperature exhaust gas flows, and the device main body on the other end portion 1b side can be exposed to the outside of the piping line. Consequently, portions preferably prevented from being exposed to the high temperature, for example, the leading terminals of the electrodes and the like can be extended to the outside of the piping line, and hence highly precise and stable measurement can be performed.

It is to be noted that the detection device main body 1 used in the particulate matter detection device needs to be provided with at least one through hole 2, and two or more through holes may be formed. Moreover, the detection device main body 1 is made of the dielectric material, whereby the pair of dust collecting electrodes 11 and 12 or various wiring lines 11b, 13b, 15b and 16b are covered with the dielectric materials, respectively.

Moreover, at least the pair of measurement electrodes 15 and 16 need to be disposed, and two or more pairs may be disposed. It is to be noted that FIG. 4 shows a case where the pair of measurement electrodes 15 and 16 are disposed in the inner side surface of the one wall of the through hole 2, but the electrodes may be embedded inside the one wall of the through hole 2.

Furthermore, there is not any special restriction on a shape of the pair of measurement electrodes, and the pair of electrodes may be disposed so that when the particulate matter is adsorbed by the wall of the through hole, the change of the electrical characteristic of the wall can be measured. It is to be noted that as shown in FIG. 7, the pair of measurement electrodes 15 and 16 preferably have a linear shape, and longly face the inner side surface or inside of the wall of the through hole 2. Moreover, the pair of linear measurement electrodes 15 and 16 may each be branched into a plurality of portions (branched into, for example, comb-like portions as shown in FIG. 7), and preferably have a plurality of facing portions (e.g., the above comb-like portions are preferably arranged so as to bite and face one another at a predetermined interval). According to such a constitution, it is possible to obtain a long (broad) portion where the pair of measurement electrodes 15 and 16 are arranged to face each other, and a more accurately measured value can be obtained.

It is to be noted that the particulate matter detection device 100a can exert the effect thereof especially when the particulate matter passing through the through hole 2 is soot discharged from the diesel engine.

[2-1a] Detection Device Main Body:

The detection device main body having one end portion thereof provided with at least one through hole and formed to be unidirectionally long is a base member of the particulate matter detection device. The detection device main body is made of the dielectric material, and at least a pair of dust collecting electrodes are disposed inside the facing walls of this through hole, respectively. The voltage can be applied across this pair of dust collecting electrodes to generate an electric field in the through hole.

The dielectric material constituting the detection device main body is preferably at least one selected from the group consisting of, for example, alumina, cordierite, mullite, glass, zirconia, magnesia and titania. Above all, alumina is preferably used. When the dust collecting electrodes are embedded inside the detection device main body made of such a dielectric material, it is possible to form the dust collecting electrodes covered with the dielectric material. Moreover, the particulate matter detection device has an excellent heat resisting property, an excellent dielectric breakdown resisting property or the like. Here, 'the dielectric material' is a substance having dielectricity prior to conductivity, and the substance behaves as an insulator with respect to a DC voltage.

It is to be noted that 'the one end portion of the detection device main body' is a region from one tip portion 1c of the detection device main body to a position corresponding to a length of 50% of the entire length of the detection device main body 1. Moreover, 'the other end portion of the detection device main body' is a region from the other tip portion 1d of the detection device main body to a position corresponding to a length of 50% of the entire length of the detection device main body 1. It is to be noted that the one end portion of the detection device main body is a region from the one tip portion 1c of the detection device main body to a position corresponding to a length of preferably 40%, further preferably 30% of the entire length of the detection device main body 1. Moreover, the other end portion of the detection device main body is a region from the other tip portion 1d of the detection device main body to a position corresponding to a length of preferably 40%, further preferably 30% of the entire length of the detection device main body 1. The position of the detection device main body 1 between the one end portion 1a and the other end portion 1b is a portion of the detection device main body 1 excluding regions of the one end portion 1a and the other end portion 1b therefrom (see FIG. 3A to FIG. 3C).

In the particulate matter detection device 100a shown in FIG. 3A to FIG. 3D, the detection device main body 1 is formed to be unidirectionally long, and there is not any special restriction on the length of the main body in a longitudinal direction, but the main body preferably has such a length that when the main body is inserted into an exhaust gas piping line, the particulate matter in the exhaust gas can efficiently be sampled.

Moreover, there is not any special restriction on the thickness of the detection device main body 1 (the length thereof in a direction (a thickness direction) vertical to both 'the longitudinal direction of the detection device main body' and 'a gas flowing direction'), but the thickness is preferably from about 0.5 to 3 mm. Here 'the thickness of the detection device main body 1' is the thickness of the thickest portion in the thickness direction. Moreover, there is not any special restriction on the length of the detection device main body 1 in the flowing direction of the gas flowing through the through hole 2 (the length thereof in the gas flowing direction), but the length is preferably, for example, from about 2 to 20 mm. Furthermore, the length of the detection device main body 1 in the longitudinal direction is preferably from 10 to 100 times the thickness of the detection device main body 1, and is preferably from 3 to 100 times the length of the detection device main body 1 in the gas flowing direction.

As shown in FIG. 3A to FIG. 3D, the detection device main body 1 has a plate-like shape with a rectangular sectional shape which is perpendicular to the longitudinal direction, and the sectional shape may be a circular or elliptic rod-like shape or the like. The main body may have another shape as long as the main body is unidirectionally long.

In the particulate matter detection device 100a, there is not any special restriction on the shape and size of the through hole 2 as long as the exhaust gas can be passed through the through hole and the amount of the particulate matter can be measured. The length of the through hole 2 in the longitudinal direction of the detection device main body is, for example, preferably from about 2 to 20 mm, and the width of the portion of the through hole 2 sandwiched between the dust collecting electrodes 11 and 12 (the length of the detection device main body in the direction vertical to both the longitudinal direction thereof and the gas flowing direction) is preferably from about 3 to 30 mm.

When the size of the through hole 2 is set to the above range, the exhaust gas containing the particulate matter can sufficiently flow through the through hole 2. Furthermore, the electric field generated in the dust collecting electrodes 11 and 12 can effectively adsorb the particulate matter in the through hole 2.

Moreover, as to the shape of the through hole 2, at least one of an inlet portion of the through hole 2 through which the fluid flows into the through hole and an outlet portion of the through hole through which the fluid flows out of the through hole is preferably enlarged. When at least one of the inlet portion of the through hole 2 through which the fluid flows into the through hole and the outlet portion of the through hole through which the fluid flows out of the through hole is enlarged, the exhaust gas flowing through the piping line can more efficiently flow into the through hole of the particulate matter detection device (in a case where the inlet portion is enlarged) or flow out of the through hole (in a case where the outlet portion is enlarged).

Furthermore, in such a particulate matter detection device, the detection device main body 1 is preferably formed by laminating a plurality of tape-like ceramic materials (ceramic sheets). In consequence, the plurality of tape-like ceramic materials can be laminated while sandwiching each electrode, wiring line and the like between the ceramic materials, to prepare the particulate matter detection device. Therefore, the particulate matter detection device can efficiently be manufactured.

[2-1b] Measurement Electrode (Electrode Portion):

At least a pair of measurement electrodes are disposed in the inner side surface or inside of the one wall of the through hole, whereby the particulate matter contained in the exhaust gas passing through the exhaust system is detected on the basis of the change of the electrical characteristic of the wall of the through hole which is caused by electrically adsorbing the particulate matter onto the wall face of the through hole by the dust collecting electrodes. Moreover, in the particulate matter detection device 100a shown in FIG. 3A to FIG. 3D, after removing the particulate matter attached to the pair of measurement electrodes 15 and 16, the electrical characteristic is measured, and the measured electrical characteristic can be compared with the initial electrical characteristic measured in the initial stage of the device to judge whether or not the device has the abnormality.

There is not any special restriction on the shape of the measurement electrodes as long as the change of the electrical characteristic of the wall of the through hole can be measured as described above, but preferable examples of the shape include a branched comb-like shape shown in FIG. 7. According to such a constitution, more accurate measurement can be performed.

There is not any special restriction on the thickness of the measurement electrode, and the thickness is, for example, preferably from 5 to 30 μm. Moreover, examples of the material of the measurement electrode include platinum (Pt), molybdenum (Mo) and tungsten (W).

The measurement electrodes are electrically connected to a pair of electrode wiring lines extending toward the other end portion of the detection device main body, respectively. There is not any special restriction on the width of each measurement electrode wiring line, and the width is, for example, preferably from about 0.2 to 1 mm. Moreover, there is not any special restriction on the thickness of the measurement electrode wiring line, and the thickness is, for example, preferably from about 5 to 30 μm. Moreover, examples of the material of the measurement electrode wiring line include platinum (Pt), molybdenum (Mo) and tungsten (W).

Furthermore, as shown in FIG. 3A to FIG. 3D, the pair of measurement electrodes 15 and 16 of the particulate matter detection device 100a comprise the electrode leading terminals 15a and 16a in the other end portion 1b of the detection device main body 1, respectively. When the abnormality judgment is performed, the electrical characteristic can be measured by the leading terminals 15a and 16a. That is, the leading terminals 15a and 16a are electrically connected to the detection means 23 (see FIG. 1A) for detecting the particulate matter and the abnormality judgment means 26 (see FIG. 1A) for performing the abnormality judgment, respectively.

When the leading terminals 15a and 16a of the pair of measurement electrodes 15 and 16 are disposed in the other end portion 1b of the detection device main body 1, a large space can be obtained between a portion where the through hole 2 is disposed (i.e., the one end portion 1a) and the leading terminals 15a and 16a. Therefore, it is possible to insert the only one end portion 1a provided with the through hole 2 and the like into the piping line through which the high-temperature exhaust gas flows, while the other end portion 1b side provided with the leading terminals 15a and 16a is extended to the outside of the piping line. If the leading terminals 15a and 16a have a high temperature, precision of the detection of the particulate matter deteriorates, and stable detection cannot easily be performed sometimes. Moreover, in case of use over a long period of time, a contact defect between an electric terminal and a harness connected to the outside occurs, and measurement cannot be performed sometimes. Therefore, the leading terminals 15a and 16a are extended to the outside of the piping line, and prevented from being exposed to the high temperature, which enables the highly precise and stable detection of the particulate matter.

As shown in FIG. 3B, the leading terminals 15a and 16a disposed in the other end portion 1b of the detection device main body 1 are preferably arranged to extend along the side surface of the other end portion 1b of the detection device main body 1 in the longitudinal direction. It is to be noted that in FIG. 3B, the other end portion 1b of the detection device main body 1 has a narrowed width, but the width of the other end portion 1b may be narrowed in this manner or does not have to be narrowed. There is not any special restriction on the shape and size of the leading terminals 15a and 16a. For example, the leading terminal preferably has a strip-like shape with a width of 0.1 to 2.0 mm and a length of 0.5 to 20 mm. Examples of the material of the leading terminals 15a and 16a include nickel (Ni), platinum (Pt), chromium (Cr), tungsten (W), molybdenum (Mo), aluminum (Al), gold (Au), silver (Ag) and copper (Cu).

[2-1c] Dust Collecting Electrode (Electrode Portion):

The dust collecting electrodes are embedded in the facing walls of the through hole and outside the position of the wall of the through hole where the above pair of measurement electrodes are embedded, and covered with the dielectric material constituting the particulate matter detection device. A predetermined voltage can be applied across the dust collecting electrodes 11 and 12 to generate the electric field in the through hole 2.

There is not any special restriction on the shape of the dust collecting electrode as long as the dust collecting electrode is embedded in the wall of the through hole and can generate the electric field in the through hole 2. In the particulate matter detection device of the present embodiment, as shown in FIG. 5, one of the dust collecting electrodes is the high-voltage dust collecting electrode 11 which is disposed in the wall opposite to the wall provided with the measurement electrodes 15 and 16 via the through hole 2 (see FIG. 4) and to which a high voltage is applied. Moreover, as shown in FIG. 8, the other dust collecting electrode is the grounded dust collecting electrode 12 disposed in the wall on the same side as the wall provided with the measurement electrodes 15 and 16 (see FIG. 4). There is not any special restriction on the thickness of each dust collecting electrode, and the thickness is, for example, preferably from 5 to 30 μm. Moreover, examples of the material of the dust collecting electrode include platinum (Pt), molybdenum (Mo) and tungsten (W).

There is not any special restriction on the shape and size of the dust collecting electrodes 11 and 12 as long as the electric field can be generated in the through hole 2. Examples of the shape include a rectangular shape, a circular shape and an oblong shape. Moreover, the size of the dust collecting electrodes 11 and 12 is preferably 70% or more of the area of the through hole 2 seen from the side surface thereof.

For example, FIG. 5 shows an example where the high-voltage dust collecting electrode 11 is formed in a size substantially equal to that of the through hole. The high-voltage dust collecting electrode 11 is connected to the wiring line 11b extending in the longitudinal direction of the detection device main body 1. The tip portion of the wiring line 11b (the tip portion of the wiring line on a side on which the wiring line is not connected to the electrode 11) is interlayer-connected (via connection) to the leading terminal 11a shown in 3B. There is not any special restriction on the width of the wiring line 11b, and the width is, for example, preferably from 0.2 to about 1 mm. Moreover, there is not any special restriction on the thickness of the wiring line 11b, and the thickness is, for example, preferably from about 5 to 30 μm. Furthermore, examples of the material of the wiring line 11b include platinum (Pt), molybdenum (Mo) and tungsten (W).

It is to be noted that both the leading terminals of the pair of dust collecting electrodes may be disposed in the other end portion of the detection device main body, but as shown in FIG. 3A to FIG. 3D, the leading terminal 12a of the grounded dust collecting electrode (the ground dust collecting electrode 12) is preferably disposed in the other end portion 1b of the detection device main body 1, whereas the leading terminal 11a of the high-voltage dust collecting electrode 11 is disposed at a position between the one end portion 1a and the other end portion 1b of the detection device main body 1. In consequence, the leading terminal 12a of the ground dust collecting electrode 12 and the leading terminal 11a of the high-voltage dust collecting electrode 11 can be disposed with a space therebetween. Therefore, when the voltage is applied across the leading terminal 11a and the leading terminal 12a to apply the voltage across the pair of dust collecting electrodes 11 and 12, arc creepage can effectively be prevented from occurring on the surface of the detection device main body 1.

In the particulate matter detection device 100a, a distance between the leading terminal 11a and the leading terminal 12a is preferably from 5 to 100 mm, further preferably from 10 to 70 mm. When the distance is shorter than 5 mm, the short circuit due to the arc creepage easily occurs sometimes. On the other hand, when the distance is longer than 100 mm and the detection device main body 1 of the particulate matter detection device 100a is disposed in the piping line or the like so that the leading terminal 11a is positioned outside the piping line, a portion of the detection device main body 1 projecting to the outside of the piping line becomes excessively long. It sometimes becomes difficult to dispose the detection device main body 1 in a small space.

Moreover, a distance between the through hole 2 and the leading terminal 11a disposed at the position between the one end portion 1a and the other end portion 1b of the detection device main body 1 is preferably 10 mm or more, further preferably 20 mm or more. When the distance is shorter than 10 mm and the particulate matter detection device 100a is disposed in the piping line so as to insert the portion of the through hole 2 into the piping line, the leading terminal 11a is easily influenced by heat of the high-temperature exhaust gas flowing through the piping line sometimes.

There is not any special restriction on the shape and size of the leading terminal 11a of the high-voltage dust collecting electrode 11. The terminal preferably has a polygonal shape such as a quadrangular shape with a width of 0.5 to 3 mm and a length of 0.5 to 3 mm, but the terminal may have a round shape, an elliptic shape, a race track shape or another shape. Examples of the material of the leading terminal 11a include nickel (Ni), platinum (Pt), chromium (Cr), tungsten (W), molybdenum (Mo), aluminum (Al), gold (Au), silver (Ag), copper (Cu), stainless steel and Kovar.

A distance between the high-voltage dust collecting electrode 11 and the through hole 2 and a distance between the ground dust collecting electrode 12 and the through hole 2 are preferably from 50 to 500 μm, further preferably from 100 to 300 μm. In such a range, the electric field can effectively be generated in the through hole. A distance between each dust collecting electrode 11 or 12 and the through hole 2 corresponds to the thickness of the portion of the dielectric material covering the dust collecting electrode 11 or 12, which faces the through hole 2.

Conditions of the electric field generated by the dust collecting electrodes change in accordance with a gap (a distance between the pair of dust collecting electrodes) or a gas temperature, but are preferably from 50 to 200 kV/cm.

The particulate matter detection device 100a electrically adsorbs the particulate matter contained in the fluid (i.e., the exhaust gas) flowing into the through hole 2 by the wall face of the through hole 2, and reads the change of the electrical characteristic due to the adsorption of the particulate matter, to detect the particulate matter contained in the exhaust gas. When the particulate matter in the exhaust gas is already charged before flowing into the through hole 2, the particulate matter is adsorbed by the electric field generated in the through hole 2. On the other hand, when the particulate matter is not charged, the particulate matter is charged by the electric field generated in the through hole 2, and the charged particulate matter is electrically adsorbed by the wall face of the through hole 2.

[2-1d] Detection Means:

The detection means detects the electrical characteristic of the electrode portion. Specifically, when the electrical characteristic to be measured is, for example, the capacitance, LCR Meter 4263B manufactured by Agilent Technologies Co., Ltd. or the like may be used.

In the particulate matter detection device 100a shown in FIG. 3A to FIG. 3D, the leading terminals 15a and 16a of the measurement electrodes 15 and 16 are electrically connected to the detection means 23 (see FIG. 1A), whereby the electrical characteristic of the measurement electrodes 15 and 16 can be detected.

[2-1e] Heating Portion (Removal Means):

The particulate matter detection device 100a shown in FIG. 4 and FIG. 9 comprises the heating portion 13 disposed (embedded) in the detection device main body 1 so as to extend along the wall face of the through hole 2 (the wall face parallel to the side surface of the detection device main body 1). The heating portion 13 corresponds to the removal means 25 of the present invention, and the device can be heated by the heating portion 13 to heat and oxidize the particulate matter adsorbed by the wall of the through hole 2 (i.e., the device can be regenerated). Moreover, during the mass measurement of the particulate matter or the like, a temperature of an internal space of the through hole 2 is adjusted to a desirable temperature, and the temperature adjustment can be performed so as to stably measure the change of the electrical characteristic of the wall of the through hole 2. Moreover, the temperature of the detection device main body 1, i.e., the dielectric material can be changed by utilizing the heating portion 13, and a relation between the temperature of the dielectric material and the capacitance of the pair of measurement electrodes can be inspected.

The heating portion 13 may be a broad film-like portion, but as shown in FIG. 9, a linear metal material is preferably disposed in a corrugated manner so that a tip portion thereof U-turns. According to such a shape, the inside of the through hole can evenly be heated to remove the particulate matter attached to the electrode portion 21 (the measurement electrodes 15 and 16). Examples of the material of the heating portion 13 include platinum (Pt), molybdenum (Mo) and tungsten (W). The heating portion 13 is preferably embedded in the detection device main body 1 so as to extend along the wall face of the through hole 2, but as shown in FIG. 9, the position of the heating portion is not limited to a position where the through hole 2 is disposed, and the heating portion may be formed so as to further extend to the other end portion 1b side of the detection device main body 1. In consequence, a temperature difference between the inside of the through hole and the periphery of the through hole can be decreased. There is an advantage that even when the device is rapidly heated, an element (the detection device main body) does not easily break down. The heating portion can preferably raise the temperature of the internal space of the through hole to 650° C.

Moreover, FIG. 9 shows an example where two wiring lines are two heating portions 13, but one heating portion may be disposed, and three or more heating portions may be disposed. Moreover, the heating portions may be disposed in both the walls of the through hole (not shown). That is, the arrangement and number of the heating portions are those necessary for achieving purposes such as the oxidation removal of the collected particulate matter and the temperature adjustment.

Moreover, the heating portion 13 shown in FIG. 9 is connected to wiring lines 13b, and as shown in FIG. 3C, the wiring lines 13b are interlayer-connected to leading terminals 13a, respectively. The leading terminals 13a of the heating portion 13 are preferably disposed in the other end portion 1b of the detection device main body 1 so as to avoid the influence of the heat when the detection device main body 1 on the one end portion 1a side is heated, in the same manner as in the leading terminals 15a and 16a of the measurement electrodes 15 and 16. In FIG. 3C, four leading terminals 13a are arranged side by side on the other side surface side of the detection device main body 1, but the arrangement of the leading terminals 13a is not limited to such arrangement.

[2-1f] Abnormality Judgment Means:

The abnormality judgment means compares the initial electrical characteristic with the electrical characteristic measured after the regeneration to judge whether or not the particulate matter detection device has the abnormality. Specifically, the means is constituted of, for example, a measuring portion which measures the electrical characteristic after the regeneration, and a judgment portion for performing the abnormality judgment.

As the measuring portion which measures the electrical characteristic after the regeneration, a portion having a constitution similar to the above detecting portion of the detection means may be used. That is, the detecting portion of the detection means may be used to measure the electrical characteristic. When the electrical characteristic to be measured is, for example, the capacitance, LCR Meter 4263B manufactured by Agilent Technologies Co., Ltd. or the like may be used.

Moreover, the judgment portion for performing the abnormality judgment may comprise, for example, an integrated circuit which performs calculation processing of calculating a difference (the change) between the value of the initial electrical characteristic and the value of the electrical characteristic measured after the regeneration to select a matching abnormality from the preset abnormality types in accordance with this change, and a display portion such as a display which displays the selected abnormality.

[3] Inspection Method of the Particulate Matter Detection Device

Next, one embodiment of an inspection method of the particulate matter detection device of the present invention will be described. The inspection method of the particulate matter detection device of the present embodiment is an inspection method of performing the abnormality judgment of the above-mentioned particulate matter detection device of the present embodiment to inspect the particulate matter detection device for the abnormality.

That is, the inspection method of the particulate matter detection device of the present embodiment is the inspection method for inspecting the particulate matter detection device 100 for the abnormality. The particulate matter detection device comprises the electrode portion 21 disposed in the exhaust system 31 of the internal combustion engine 30 and the detection means 23 for detecting the electrical characteristic of the electrode portion 21 as shown in FIG. 1A and FIG. 1B, whereby the particulate matter 36 contained in the exhaust gas 32 passing through the exhaust system 31 is detected on the basis of the change of the electrical characteristic due to the particulate matter 36 attached to the electrode portion 21.

The inspection method of the particulate matter detection device of the present embodiment comprises the steps of measuring the electrical characteristic of the electrode portion 21 in a use initial state where the particulate matter 36 is not attached to the electrode portion 21 to obtain the electrical characteristic as an initial electrical characteristic; measuring the electrical characteristic of the electrode portion 21 in a state where as shown in FIG. 1B, the particulate matter 36 attached to the electrode portion 21 of the particulate matter detection device 100 installed in a through channel (the exhaust system 31) through which the exhaust gas 32 passes is removed to start the detection of the particulate matter by the particulate matter detection device 100; and comparing a value of the measured electrical characteristic with a value of the initial electrical characteristic to judge whether or not the particulate matter detection device 100 has an abnormality.

It is to be noted that the detection of the particulate matter is performed by the detection means 23, the removal of the particulate matter (the regeneration) is performed by the removal means 25, and the abnormality judgment is performed by the abnormality judgment means 26.

According to such a constitution, it can be judged whether or not the detection of the particulate matter is normally performed, to satisfactorily inspect the device for break-down or defect. For example, when the exhaust gas treatment device normally functions, it can be confirmed whether or not normal measurement is performed at the present moment in the detection device which does not receive any signal concerning the detection or the detection device which receives a remarkably small signal indicating 'non-detected' if the signal is received and which recognizes that the signal is first detected if the signal is detected. Therefore, it is possible to simply confirm a zero point of the particulate matter detection device and also confirm a defect (an abnormality) such as the break-down of the detection device.

Moreover, in the inspection method of the particulate matter detection device of the present embodiment, it is possible to limit or specify a place where the defect has occurred or contents of the defect in accordance with the obtained electrical characteristic value. Therefore, when the defect occurs, it is possible to simply and readily perform an operation such as replacement or repair of a defective portion.

It is to be noted that in the inspection method of the particulate matter detection device of the present embodiment (hereinafter referred to simply as 'the inspection method' sometimes), as described above, a device further comprising removal means for removing the particulate matter attached to the device is preferably used as the particulate matter detection device. It is to be noted that as such removal means, for example, a heater which heats the inside of the device may be used. Alternatively, in the inspection method of the present embodiment, the removal means is not disposed in the particulate matter detection device, but, needless to say, the abnormality judgment may be performed by using separate removal means for removing the particulate matter.

Moreover, in the inspection method of the present embodiment, the capacitance or the resistance is preferably measured as the electrical characteristic. According to such a constitution, the detection of the particulate matter and the abnormality judgment can be performed in accordance with the same type of electrical characteristic (i.e., the capacitance or the resistance), and the abnormality judgment can more simply be performed.

Furthermore, in the inspection method of the present embodiment, the particulate matter detection device as an inspection target is preferably a particulate matter detection device in which an initial capacitance as the initial electrical characteristic is set to a range of 0 to 100 pF. In the particulate matter detection device having the above constitution, heretofore, it has been remarkably difficult to perform the abnormality judgment, but the abnormality judgment can accurately and simply be performed by using the inspection method of the present embodiment.

Moreover, the inspection method of the present embodiment can be applied to inspect the device for various abnormalities by setting a judgment standard similar to that of the above particulate matter detection device of the present embodiment. The abnormality judgment differs with, for example, the constitution of the particulate matter detection device for performing the abnormality judgment. However, when the electrical characteristic to be compared during the abnormality judgment is the capacitance and the value of the measured capacitance is 0 pF, it can be judged that the abnormality is the disconnection or contact defect of the electrode portion. Moreover, when the electrical characteristic to be compared during the abnormality judgment is similarly the capacitance and the value of the initial capacitance as the initial electrical characteristic is compared with the value of the measured capacitance (the electrical characteristic after the regeneration) to obtain a difference of 0.5 pF or more, it can be judged that the abnormality is at least one abnormality selected from the group consisting of the break-down of the electrode portion, the short circuit of a pair of electrode portions in a case where the pair of electrode portions are used, and the break-down of a dielectric material in a case where at least a part of the electrode portion is covered with the dielectric material. In this way, according to the inspection method of the present embodiment, it is possible to limit or specify, to some extent, the type of the abnormality and the place of the occurring abnormality in the particulate matter detection device, in accordance with the obtained electrical characteristic value.

Furthermore, in the inspection method of the present embodiment, a particulate matter detection device in which at least a part of the electrode portion is covered with the dielectric material is used as the particulate matter detection device, and the electrical characteristic of the electrode portion may be measured while raising a temperature of the dielectric material to further inspect the device for the disconnection or contact defect of the electrode portion or the break-down of the dielectric material, in accordance with the change of the electrical characteristic to be measured. That is, during the measurement of the electrical characteristic, the measurement is performed while raising the temperature of the dielectric material, whereby further detailed abnormality judgment can be performed. For example, when the electrical characteristic to be measured does not change with respect to the temperature change of the dielectric material, it can be judged that the abnormality is the disconnection or contact defect of the electrode portion.

Additionally, in the inspection method of the present embodiment, during the measurement of the electrical characteristic of the electrode portion, the electrical characteristic is measured while changing a frequency of a voltage to be applied to the electrode portion. The device may be inspected for the break-down of the dielectric material in accordance with transition of the electrical characteristic to be measured.

When the temperature of the dielectric material is raised or the frequency of the voltage is changed as described above, the change of the electrical characteristic due to a specific abnormality can intentionally be increased, for example, in a case where the change of the electrical characteristic due to the specific abnormality occurs, which does not occur in the usual measurement of the electrical characteristic, or the abnormality is so remarkably small that it is difficult to perform judgment of an abnormality difference in the usual measurement of the electrical characteristic. In consequence, the abnormality judgment can be performed in more detail and in a broader range.

Also in the inspection method of the present embodiment, instead of the measurement of the initial capacitance, the initial electrical characteristic suitable for the constitution of the particulate matter detection device may beforehand be set, and the value of the set initial electrical characteristic may be compared with the value of the measured electrical characteristic to inspect the particulate matter detection device for abnormality. That is, the initial electrical characteristic is the judgment standard for performing the abnormality judgment and, accordingly, has a peculiar value in accordance with the constitution of the device. Therefore, in a case where a plurality of particulate matter detection devices having the same constitution are manufactured or the like, the initial electrical characteristic is beforehand known. Therefore, in each device, the initial electrical characteristic is not measured, but the abnormality judgment may be performed by using the value of the beforehand known initial electrical characteristic.

Moreover, in the inspection method of the present embodiment, as the particulate matter detection device, there is preferably used, for example, a particulate matter detection device further comprising a unidirectionally long detection device main body having one end portion thereof provided with at least one through hole. The electrode portion comprises at least a pair of measurement electrodes disposed in the inner side surface or inside of one wall of the through hole; and at least a pair of dust collecting electrodes embedded in the facing walls of the through hole, respectively, and outside the position of the wall of the through hole where the pair of measurement electrodes are embedded, and covered with the dielectric material. Examples of such a particulate matter detection device include the particulate matter detection device 100a shown in FIG. 3A to FIG. 3D.

When the particulate matter detection device 100a shown in FIG. 3A to FIG. 3D is the inspection target, the initial electrical characteristic can be compared with the value of the measured electrical characteristic to inspect the device for at least one type of abnormality selected from the group consisting of the disconnection, contact defect and break-down of the measurement electrode 15 or 16, the short circuit of the pair of measurement electrodes 15 and 16 and the break-down of the dielectric material.

It is to be noted that the inspection method of the present embodiment comprises the steps of obtaining an electrical characteristic measured in a use initial state where any particulate matter is not attached to an electrode portion as an electrical characteristic which is a reference; measuring the electrical characteristic of the electrode portion after removing the particulate matter attached to the electrode portion of the particulate matter detection device as the inspection target (after regenerating the device); and comparing the measured electrical characteristic with the above initial electrical characteristic to judge whether or not the device has an abnormality. In this case, the type and measurement method of the electrical characteristic and the like are not limited to those described above. Moreover, the abnormality judgment may be performed by using the abnormality judgment method described above in the particulate matter detection device of the present embodiment as an abnormality judgment method.

EXAMPLES

Hereinafter, the present invention will further specifically be described with respect to examples, but the present invention is not limited to these examples.

(Preparation of Particulate Matter Detection Device)

As an inspection target for performing an inspection method of a particulate matter detection device of the present invention, a particulate matter detection device 100a shown in FIG. 3A to FIG. 3D and FIG. 4 to FIG. 9 was prepared.

Specifically, first, alumina was used as a dielectric material, polyvinyl butyral was used as a binder, di-2-ethylhexyl phthalate was used as a plasticizer, sorbitan tri-oleate was used as a dispersant, and an organic solvent (xylene:butanol=6:4 (mass ratio)) was used as a dispersion medium. These materials were placed and mixed in an alumina pot, to prepare a slurried forming material for forming a green sheet. As to usages of the raw materials, with respect to 100 parts by mass of alumina, 7 parts by mass of binder, 3.5 parts by mass of plasticizer, 1.5 parts by mass of dispersant and 100 parts by mass of organic solvent were used.

Next, the obtained slurried forming material for preparing the green sheet was stirred under a reduced pressure, defoamed and prepared so as to obtain a viscosity of 4 Pa·s. The viscosity of the slurry was measured by a B-type viscometer.

Next, the slurried forming material obtained by the above method was processed in a sheet-like shape by use of a doctor blade process. At this time, the green sheet provided with a cut portion was prepared so that a through hole is formed in laminated green sheets. As to the thicknesses of the green sheets, the thickness of the green sheet provided with measurement electrodes was set to 50 μm, and the thicknesses of the other green sheets were set to 250 μm.

On the surface of the obtained green sheet, as shown in FIG. 4 to FIG. 9, electrodes (the measurement electrodes and dust collecting electrodes), a heating portion (removal means), wiring lines and leading terminals were formed. A conductive paste for forming the electrodes, a ground electrode, the wiring lines and attachment terminals to be arranged was prepared by adding, to platinum powder, 2-ethylhexanol as a solvent, polyvinyl butyral as a binder, di-2-ethylhexyl phthalate as a plasticizer, sorbitan tri-oleate as a dispersant, alumina as a co-material of the green sheet and glass frit as a sintering aid, and sufficiently kneading the materials by use of a stone mill and a tri-roll mill (platinum:alumina:glass frit:2-ethylhexanol:polyvinyl butyral: di-2-ethylhexyl phthalate:sorbitan tri-oleate=80:15:5:50:7:3.5:1 in terms of a mass ratio).

Moreover, a conductive paste for forming the heating portion was prepared by adding, to platinum powder, 2-ethylhexanol as a solvent, polyvinyl butyral as a binder, di-2-ethylhexyl phthalate as a plasticizer, sorbitan tri-oleate as a dispersant, alumina as a co-material of the green sheet and glass frit as a sintering aid, and sufficiently kneading the materials by use of a stone mill and a tri-roll mill (platinum:alumina:glass frit:2-ethylhexanol:polyvinyl butyral: di-2-ethylhexyl phthalate:sorbitan tri-oleate=80:15:5:50:7:3.5:1 in terms of a mass ratio).

The conductive paste formed in this manner was printed on the surface of the green sheet by screen printing to form an electrode having a predetermined shape and the like thereon. Specifically, as to two green sheets among a plurality of green sheets, dust collecting electrodes were disposed on one surface of each of the green sheets, and a wiring line extending from the high-voltage dust collecting electrode to the other end portion was disposed, to form the two green sheets provided with the dust collecting electrodes.

Furthermore, a pair of comb-like measurement electrodes were formed in a portion where a through hole was to be formed in the green sheet having a thickness of 50 μm. The pair of comb-like measurement electrodes were arranged to bite and face each other with a space being left therebetween so that a comb portion pitch was 0.35 mm (a comb portion clearance was 0.15 mm and a comb portion width was 0.20 mm).

Furthermore, a through-hole forming cut portion was formed in a position of another green sheet which position superimposes onto the measurement electrodes when the green sheet was superimposed onto the green sheet provided with the measurement electrodes, to form the green sheet provided with the cut portion. In addition, the heating portion was formed in a position of still another green sheet which position superimposes onto the through-hole forming cut portion when the green sheet was superimposed onto the green sheet provided with the cut portion, and a wiring line was disposed so as to extend from the heating portion to the other end portion, thereby forming the green sheet provided with the heating portion.

Subsequently, another green sheet which was not provided with any electrode or the like was superimposed onto each of the two green sheets provided with the dust collecting electrodes so as to cover the dust collecting electrodes and the wiring line with the green sheets, thereby forming the dust collecting electrodes-embedded green sheets. Moreover, the green sheets were laminated so that the green sheet provided with the measurement electrodes and the green sheet provided with the cut portion were sandwiched between the two dust collecting electrodes-embedded green sheets. Furthermore, the green sheets were laminated so that the green sheet provided with the heating portion was positioned outside the dust collecting electrodes-embedded green sheets, thereby forming a green sheet laminate having a state where the cut portion was sandwiched between the two dust collecting electrodes and the measurement electrodes were sandwiched between the two wiring lines. The respective wiring lines and leading terminals corresponding to the wiring lines were interlayer-connected (via connection) by a conductive paste embedding process.

To laminate the green sheets, the green sheets were pressurized and laminated by using a uniaxial press machine which could heat the green sheets, to obtain a non-fired body of a particulate matter detection device comprising the green sheet laminate.

The obtained green sheet laminate (the non-fired body of the particulate matter detection device) was dried at 120° C. and fired at 1500° C. to prepare the particulate matter detection device. The leading terminals of the particulate matter detection device were electrically connected to LCR Meter (LCR Meter 4263B manufactured by Agilent Technologies Co., Ltd.) as detection means and abnormality judgment means via wiring lines. The particulate matter detection device prepared in this manner was a detection device (1).

It is to be noted that as judgment standards of the abnormality judgment means in the detection device (1), judgment standards (a) to (c) were set as follows, and a matching abnormality was selected by the abnormality judgment means to perform abnormality judgment.

(a): A value of an initial capacitance as an initial electrical characteristic was compared with a value of a measured capacitance, and when a difference between the values was less than 0.5 pF, it was judged that there was not any abnormality.

(b): When the value of the measured capacitance was 0 pF, it was judged that the abnormality was the disconnection or contact defect of an electrode portion.

(c): The value of the initial capacitance as the initial electrical characteristic was compared with the value of the measured capacitance, and when the difference between the values was 0.5 pF or more, it was judged that the abnormality was at least one selected from the group consisting of break-down of the electrode portion, short circuit of a pair of electrode portions and break-down of the dielectric material (with the proviso that when the difference was 1000 pF or more, the abnormality was judged to be the short circuit of the pair of electrode portions).

Moreover, as particulate matter detection devices in addition to the above particulate matter detection device, there were prepared a detection device (2) in which a measurement electrode was disconnected, a detection device (3) in which a pair of measurement electrodes were disconnected, a detection device (4) in which a dielectric material had cracks due to shock, and a detection device (5) in which a wiring line between the detection device (an electrode portion, specifically a measurement electrode) and detection means (specifically, a circuit constituting the detection means) was disconnected.

Example 1

Abnormality judgment was performed with respect to the above detection device (1) by abnormality judgment means. Specifically, first, an initial capacitance of the detection device (1) was measured on conditions of 1 Vrms and 1 kHz. The measured initial capacitance was 6.5 pF.

Next, a diesel particulate filter was disposed in an exhaust system of a diesel engine, and the detection device (1) was further installed on the downstream side of the filter, to detect a particulate matter. After using the detection device (1) for one hour, the particulate matter attached to the detection device (1) was removed. After regenerating the detection device (1) in such a state as to start the inspection of the particulate matter, the capacitance between a pair of measurement electrodes was measured again. The measured capacitance was 6.5 pF.

Since the initial capacitance and the measured capacitance had an equal value, it was judged that the detection device (1) matched the above judgment standard (a) of abnormality judgment means and that any abnormality did not occur in the detection device. Moreover, the detection device (1) was taken out of the exhaust system, and the state of the device was confirmed in detail. It was confirmed that the taken device had a normal function, and any abnormality was not found.

Example 2

The above detection device (2) was installed in an exhaust system of a diesel engine to detect a particulate matter in the same manner as in Example 1. Furthermore, after regenerating the device (1), a capacitance between a pair of measurement electrodes was measured again. The measured capacitance was 3 pF. It is to be noted that since the detection device (2) had a constitution similar to the detection device (1) except that an abnormality was intentionally caused, and hence an initial capacitance was set to 6.5 pF in the same manner as in Example 1.

When the value of the initial capacitance was compared with the value of the measured capacitance, a decrease of 2.5 pF and a change of 0.5 pF or more were seen, and it was judged that the device had the abnormality (the judgment standard (b)). In case of a change of 0.5 pF or more, one of abnormalities such as break-down and short circuit of an electrode portion and break-down of a dielectric material was presumed. However, in case of the short circuit, the measured capacitance had a remarkably large value (e.g., 1000 pF or more). Therefore, it was judged that the abnormality was disconnection of a measurement electrode as the break-down of the electrode portion.

Examples 3 to 5

The above detection devices (3) to (5) were also installed in an exhaust system of a diesel engine to detect a particulate matter in the same manner as in Example 1. Furthermore, after regenerating each device, a capacitance between a pair of measurement electrodes was measured again. In the detection device (3), the measured capacitance was 1000 pF or more. In the detection device (4), the measured capacitance was 5.5 pF. In the detection device (5), the measured capacitance was 0 pF.

In the detection device (3), an initial capacitance was 6.5 pF, whereas the measured capacitance was 1000 pF or more. It was judged that abnormality of short circuit of a measurement electrode (provision of the judgment standard (c)) occurred.

Moreover, in the detection device (4), an initial capacitance was 6.5 pF, whereas a decrease of 1.0 pF and a change of 0.5 pF or more were seen. Therefore, it was judged that an abnormality occurred (the judgment standard (c)).

Furthermore, in the detection device (5), the measured capacitance was 0 pF, and a capacitance after regeneration was not measured. Therefore, it was judged that an abnormality of the judgment standard (b), i.e., the disconnection or contact defect of an electrode portion occurred. In the detection device (5), since the capacitance was not measured at all, disconnection of a wiring line from a measurement electrode to detection means and abnormality judgment means was presumed.

(Result)

The particulate matter detection device of the present invention can judge whether or not the device has the abnormality, from the value of the initial capacitance and the value of the measured capacitance. In particular, the judgment standard corresponding to the device was disposed, whereby as described in Examples 2 to 5, it was possible to limit or specify a place where the abnormality occurred or contents of the abnormality.

A particulate matter detection device of the present invention can be used as a detection device which detects a particulate matter in an exhaust gas discharged from an internal combustion engine. Moreover, using the particulate matter detection device of the present invention and an inspection method of the particulate matter detection device, the particulate matter detection device can judge whether or not the detection of the particulate matter is normally performed and satisfactorily inspect the device for an abnormality.

Description of Reference Numerals 1: detection device main body, 1a: one end portion, 1b: the other end portion, 1c: one tip portion, 1d: the other tip portion, 2: through hole, 11: dust collecting electrode (high-voltage dust collecting electrode), 12: dust collecting electrode (ground dust collecting electrode), 11a, 12a and 13a: leading terminal, 11b, 12b and 13b: wiring line, 13: heating portion, 15 and 16: measurement electrode, 15a and 16a: measurement electrode leading terminal (leading terminal), 15b and 16b: measurement electrode wiring line (wiring line), 21: electrode portion, 23: detection means, 25: removal means, 26: abnormality judgment means, 30: internal combustion engine, 31: exhaust system, 36: particulate matter, and 100: particulate matter detection device.

What is claimed is:

1. A particulate matter detection device which comprises:
an electrode portion disposed in an exhaust system of an internal combustion engine; and
detection means for detecting an electrical characteristic of the electrode portion, whereby a particulate matter contained in an exhaust gas passing through the exhaust system is detected on the basis of a change of the electrical characteristic due to the particulate matter attached to the electrode portion,
the particulate matter detection device further comprising:
removal means for removing the particulate matter attached to the electrode portion; and
abnormality judgment means for measuring the electrical characteristic of the electrode portion in a use initial state where any particulate matter is not attached to the electrode portion, to obtain the electrical characteristic as an initial electrical characteristic, and
measuring the electrical characteristic of the electrode portion in a state where the particulate matter attached to the surface of the electrode portion is removed by the removal means to start the detection of the particulate matter by the particulate matter detection device, and comparing a value of the measured electrical characteristic with a value of the initial electrical characteristic, to judge whether or not the particulate matter detection device has an abnormality.

2. The particulate matter detection device according to claim 1, wherein the electrical characteristic compared by the abnormality judgment means is a capacitance or a resistance.

3. The particulate matter detection device according to claim 1, wherein the removal means comprises a heater which heats the inside of the device.

4. The particulate matter detection device according to claim 1, wherein at least a part of the electrode portion is covered with a dielectric material, and the abnormality judgment means measures the electrical characteristic of the electrode portion while raising a temperature of the dielectric material, and further inspects the device for disconnection or contact defect of the electrode portion or break-down of the dielectric material from the change of the electrical characteristic to be measured.

5. The particulate matter detection device according to claim 4, wherein it is judged that the abnormality is the disconnection or contact defect of the electrode portion in a case where the electrical characteristic to be measured does not change with respect to temperature change of the dielectric material.

6. The particulate matter detection device according to claim 1, wherein at least a part of the electrode portion is covered with a dielectric material, and during the measurement of the electrical characteristic of the electrode portion, the abnormality judgment means measures the electrical characteristic while changing a frequency of a voltage to be applied to the electrode portion, and inspects the device for break-down of the dielectric material in accordance with transition of the electrical characteristic to be measured.

7. The particulate matter detection device according to claim 1, wherein the initial electrical characteristic is beforehand set to the abnormality judgment means, and the abnormality judgment means compares a value of the set initial electrical characteristic with a value of the measured electrical characteristic to judge whether or not the particulate matter detection device has the abnormality.

8. The particulate matter detection device according to claim 1, further comprising:
a unidirectionally long detection device main body having one end portion provided with at least one through hole,
wherein the electrode portion comprises at least a pair of measurement electrodes disposed in the inner side surface or inside of one wall of the through hole; and at least a pair of dust collecting electrodes embedded in facing walls of the through hole, respectively, and outside a position of the wall of the through hole where the pair of measurement electrodes are embedded, and covered with the dielectric material.

9. The particulate matter detection device according to claim 8, wherein the value of the initial electrical characteristic is compared with the value of the measured electrical characteristic to inspect the device for at least one abnormality selected from the group consisting of disconnection, contact defect and break-down of the measurement electrode, short circuit of the pair of measurement electrodes and break-down of the dielectric material.

10. An inspection method of a particulate matter detection device comprising: an electrode portion disposed in an exhaust system of an internal combustion engine; and detection means for detecting an electrical characteristic of the electrode portion, whereby a particulate matter contained in an exhaust gas passing through the exhaust system is detected on the basis of a change of the electrical characteristic due to the particulate matter attached to the electrode portion,
the inspection method comprising the steps of:
measuring the electrical characteristic of the electrode portion in a use initial state where any particulate matter is not attached to the electrode portion, to obtain the electrical characteristic as an initial electrical characteristic;
measuring the electrical characteristic of the electrode portion in a state where the particulate matter attached to the electrode portion of the particulate matter detection device installed in a through channel through which the exhaust gas passes is removed to start the detection of the particulate matter by the particulate matter detection device; and
comparing a value of the measured electrical characteristic with a value of the initial electrical characteristic, to judge whether or not the particulate matter detection device has the abnormality.

11. The inspection method of the particulate matter detection device according to claim 10, which uses the particulate matter detection device further comprising removal means for removing the particulate matter attached to the device.

12. The inspection method of the particulate matter detection device according to claim 10, further comprising the steps of measuring a capacitance or a resistance as the electrical characteristic.

13. The inspection method of the particulate matter detection device according to claim 10, which uses the particulate matter detection device further comprising a heater which heats the inside of the device.

14. The inspection method of the particulate matter detection device according to claim 10, which uses the particulate matter detection device comprising the electrode portion having at least a part thereof covered with a dielectric material, further comprising the steps of measuring the electrical characteristic of the electrode portion while raising a temperature of the dielectric material, to further inspect the device for disconnection or contact defect of the electrode portion or break-down of the dielectric material from a change of the electrical characteristic to be measured.

15. The inspection method of the particulate matter detection device according to claim 14, further comprising the steps of judging that the abnormality is the disconnection or contact defect of the electrode portion in a case where the electrical characteristic to be measured does not change with respect to temperature change of the dielectric material.

16. The inspection method of the particulate matter detection device according to claim 10, which uses the particulate matter detection device comprising the electrode portion having at least a part thereof covered with a dielectric material, wherein the step of measuring the electrical characteristic of the electrode portion measures the electrical characteristic while changing a frequency of a voltage to be applied to the electrode portion, to inspect the device for break-down of the dielectric material in accordance with transition of the electrical characteristic to be measured.

17. The inspection method of the particulate matter detection device according to claim 10, instead of the step of measuring the initial capacitance, further comprising the steps of: beforehand setting an initial electrical characteristic suitable for a constitution of the particulate matter detection device; and comparing a value of the set initial electrical characteristic with a value of the measured electrical characteristic, to inspect the particulate matter detection device for the abnormality.

18. The inspection method of the particulate matter detection device according to claim 10, which uses the particulate matter detection device further comprising: a unidirectionally long detection device main body having one end portion provided with at least one through hole; and the electrode portion including at least a pair of measurement electrodes disposed in the inner side surface or inside of one wall of the through hole, and at least a pair of dust collecting electrodes embedded in facing walls of the through hole, respectively, and outside a position of the wall of the through hole where the pair of measurement electrodes are embedded, and covered with the dielectric material.

19. The inspection method of the particulate matter detection device according to claim 18, further comprising the steps of comparing a value of the initial electrical characteristic with a value of the measured electrical characteristic, to inspect the device for at least one abnormality selected from the group consisting of disconnection, contact defect and break-down of the measurement electrode, short circuit of the pair of measurement electrodes and break-down of the dielectric material.

* * * * *